US008993724B2

(12) United States Patent
Fischer et al.

(10) Patent No.: US 8,993,724 B2
(45) Date of Patent: Mar. 31, 2015

(54) PROCESS FOR THE PREPARATION OF GLYCOSYLATED INTERFERON BETA

(75) Inventors: Dina Fischer, Rehovot (IL); Alain Bernard, Brussels (BE); Paul Ducommun, Lausanne (CH); Mara Rossi, Rome (IT)

(73) Assignee: Ares Trading S.A., Aubonne (CH)

(*) Notice: Subject to any disclaimer, the term of this patent is extended or adjusted under 35 U.S.C. 154(b) by 192 days.

(21) Appl. No.: 13/159,864

(22) Filed: Jun. 14, 2011

(65) Prior Publication Data

US 2011/0305669 A1  Dec. 15, 2011

Related U.S. Application Data

(62) Division of application No. 12/064,422, filed as application No. PCT/EP2005/054220 on Aug. 26, 2005, now abandoned.

(51) Int. Cl.
A61K 38/21 (2006.01)
C07K 14/565 (2006.01)
C12P 21/04 (2006.01)
C12N 5/02 (2006.01)
C12N 5/07 (2010.01)
C12N 5/00 (2006.01)
C12N 15/00 (2006.01)

(52) U.S. Cl.
CPC ............... C12N 5/0031 (2013.01); C12N 5/06 (2013.01); C12N 15/00 (2013.01); A61K 38/215 (2013.01); C12N 2500/99 (2013.01); C07K 14/565 (2013.01); C12N 2500/12 (2013.01); C12N 2500/32 (2013.01); C12N 2510/02 (2013.01)
USPC ........ 530/351; 424/85.6; 435/69.51; 435/325

(58) Field of Classification Search
None
See application file for complete search history.

(56) References Cited

U.S. PATENT DOCUMENTS

| 5,338,835 | A | 8/1994 | Boime |
| 5,376,567 | A | 12/1994 | McCormick et al. |
| 5,405,945 | A | 4/1995 | Boime et al. |
| 5,508,261 | A | 4/1996 | Moyle et al. |
| 5,545,723 | A * | 8/1996 | Goelz et al. .................. 424/85.6 |
| 5,567,677 | A | 10/1996 | Castensson et al. |
| 5,585,345 | A | 12/1996 | Boime |
| 5,883,073 | A | 3/1999 | Boime et al. |
| 5,990,288 | A | 11/1999 | Musick et al. |
| 6,162,905 | A | 12/2000 | Lualdi et al. |
| 7,741,455 | B2 | 6/2010 | Valax et al. |
| 7,780,960 | B2 * | 8/2010 | Park et al. .................. 424/85.6 |
| 7,901,670 | B2 * | 3/2011 | Park et al. .................. 424/85.6 |
| 2003/0017550 | A1 * | 1/2003 | Pang .......................... 435/69.51 |
| 2003/0171267 | A1 | 9/2003 | Rosen et al. |
| 2003/0186893 | A1 | 10/2003 | Paradisi et al. |
| 2004/0013644 | A1 * | 1/2004 | Rasmussen et al. ......... 424/85.6 |
| 2004/0115168 | A1 * | 6/2004 | DeFrees et al. .............. 424/85.6 |
| 2005/0186664 | A1 | 8/2005 | Rosen et al. |
| 2006/0121568 | A1 * | 6/2006 | Drapeau et al. .............. 435/69.1 |
| 2007/0129295 | A1 | 6/2007 | Rossi |
| 2008/0219952 | A1 | 9/2008 | Fischer et al. |
| 2008/0280832 | A1 | 11/2008 | Muda et al. |
| 2009/0209454 | A1 | 8/2009 | Ziegler et al. |
| 2010/0249381 | A1 | 9/2010 | Delvaille et al. |
| 2010/0256337 | A1 | 10/2010 | Eon-Duval |

FOREIGN PATENT DOCUMENTS

| CA | 2399100 | 8/2001 |
| EP | 0475779 A1 | 3/1991 |
| EP | 1 106 623 | 6/2001 |
| EP | 1247818 | 10/2002 |
| EP | 1482031 A1 | 12/2004 |
| GB | 2 055 384 | 3/1981 |
| WO | WO 88/10270 | 12/1988 |
| WO | WO 94/10309 | 5/1994 |
| WO | WO 96/25496 | 8/1996 |
| WO | WO 97/29767 | 2/1997 |
| WO | WO 98/20039 | 5/1998 |
| WO | WO 98/21234 | 5/1998 |
| WO | WO 00/63248 | 10/2000 |
| WO | WO 01/58493 | 8/2001 |
| WO | WO 2004/006756 | 1/2004 |
| WO | WO 2004/050679 | 6/2004 |
| WO | WO 2005/001025 | 1/2005 |
| WO | WO 2005/020934 | 3/2005 |
| WO | WO 2005/063811 | 7/2005 |
| WO | WO 2006/016960 A2 | 2/2006 |
| WO | WO 2006/051070 | 5/2006 |

OTHER PUBLICATIONS

Chuppa, S., et al. Fermentor temperature as a tool for control of high-density perfusion cultures of mammalian cells. Biotechnol. Bioeng., 1997, vol. 55, p. 328-338.*
Bishop, L.A. et al. "Both of the β-Subunit Carbohydrate Residues of Follicle-Stimulating Hormone Determine the Metabolic Clearance Rate and in Vivo Potency" *Endocrinology*, 1995, pp. 2635-2640, vol. 136, No. 6.
Chappel, S. et al. "Follicle stimulating hormone and its receptor: future perspectives" *Human Reproduction*, 1998, pp. 18-35 and 47-51, vol. 13, Supplement No. 3.
D'Antonio, M. et al. "Biological characterization of recombinant human follicle stimulating hormone isoforms" *Human Reproduction*, 1999, pp. 1160-1167, vol. 14, No. 5.
Furuhashi, M. et al. "Effect of Additional N-Glycosylation Signal in the N-Terminal Region on Intracellular Function of the Human Gonadotropin α-Subunit" *Endocrine Journal*, Jun. 2003, pp. 245-253, vol. 50, No. 3.
Galway, A. B. et al. "In Vitro and in Vivo Bioactivity of Recombinant Human Follicle-Stimulating Hormone and Partially Deglycosylated Variants Secreted by Transfected Eukaryotic Cell Lines" *Endocrinology*, 1990, pp. 93-100, vol. 127, No. 1.

(Continued)

*Primary Examiner* — Robert Landsman
*Assistant Examiner* — Bruce D Hissong
(74) *Attorney, Agent, or Firm* — Saliwanchik, Lloyd & Eisenschenk

(57) ABSTRACT

The present invention relates to a process for the production of interferon beta, and to an interferon beta composition having a unique glycosylation pattern.

17 Claims, 7 Drawing Sheets

(56) References Cited

OTHER PUBLICATIONS

Grossman, M. et al. "Site-Directed Mutagenesis of Amino Acids 33-44 of the Common α-Subunit Reveals Different Structural Requirements for Heterodimer Expression among the Glycoprotein Hormones and Suggests that Cyclic Adenosine 3',5'-Monophosphate Production and Growth Promotion are Potentially Dissociable Functions of Human Thyrotropin" *Molecular Endocrinology*, 1996, pp. 769-779, vol. 10, No. 6.

Liu, C. et al. "Site-directed Alanine Mutagenesis of Phe$^{33}$, Arg$^{35}$, and Arg$^{42}$-Ser$^{43}$-Lys$^{44}$ in the Human Gonadotropin α-Subunit" *The Journal of Biological Chemistry*, Oct. 15, 1993, pp. 21613-21617, vol. 268, No. 29.

Perlman, S. et al. "Glycosylation of an N-Terminal Extension Prolongs the Half-Life and Increases the in Vivo Activity of Follicle Stimulating Hormone" *Journal of Clinical Endocrinology and Metabolism*, Jul. 2003, pp. 3227-3235, vol. 88, No. 7.

Roth, K.E. et al. "Scanning-alanine mutagenesis of long loop residues 33-53 in follicle stimulating hormone beta subunit" *Molecular and Cellular Endocrinology*, 1995, pp. 143-149, vol. 109.

Valove, F.M. et al. "Receptor Binding and Signal Transduction are Dissociable Functions Requiring Different Sites on Follicle Stimulating Hormone" *Endocrinology*, 1994, pp. 2657-2661, vol. 135, No. 6.

Weenen, C. et al. "Long-Acting Follicle-Stimulating Hormone Analogs Containing N-Linked Glycosylation Exhibited Increased Bioactivity Compared with O-Linked Analogs in Female Rats" *Journal of Clinical Endocrinology and Metabolism*, Oct. 2004, pp. 5204-5212, vol. 89, No. 10.

Yoo, J. et al. "COOH-terminal Amino Acids of the α Subunit Play Common and Different Roles in Human *Choriogonadotropin* and *Follitropin*" *The Journal of Biological Chemistry*, Jun. 25, 1993, pp. 13034-13042, vol. 268, No. 18.

Database Geneseq [Online], Jan. 29, 2002, "Human FSH-alpha subunit mutant D3N/Q5T", XP-002439754, Database Accession No. AAM51736, p. 1.

Database Geneseq [Online], Jan. 29, 2002, "Human FSH-alpha subunit mutant D3N/Q5S", XP-002439755, Database Accession No. AAM51735, p. 1.

Selkirk, C. "Ion-Exchange Chromatography" *Methods in Molecular Biology*, 2004, pp. 125-131, vol. 244.

Capture: In Chapter 4 of the Amersham Protein Purification Handbook, 1999, pp. 29-36.

Kastner, M. "Protein liquid chromatography" *Journal of Chromatography Library*, 2000, pp. 1-3, vol. 61.

Altschul, S. F. et al. "Basic Local Alignment Search Tool" *Journal of Molecular Biology*, 1990, pp. 403-410, vol. 215.

Altschul, S. F. et al. "Gapped BLAST and PSI-BLAST: a new generation of protein database search programs" *Nucleic Acids Research*, 1997, pp. 3389-3402, vol. 25, No. 17.

Barber, M. et al. "Fast Atom Bombardment of Solids (F.A.B.): A New Ion Source for Mass Spectrometry" *J.C.S. Chem. Comm.*, 1981, pp. 325-327.

Busslinger, M. et al. "β$^+$ Thalassemia: Aberrant Splicing Results from a Single Point Mutation in an Intron" *Cell*, Dec. 1981, pp. 289-298, vol. 27.

Chernajovsky, Y. et al. "Efficient Constitutive Production of Human Fibroblast Interferon by Hamster Cells Transformed with the IFN-β$_1$ Gene Fused to an SV40 Early Promoter" *DNA*, 1984, pp. 297-308, vol. 3, No. 4.

Chomczynski, P. et al. "Single-Step Method of RNA Isolation by Acid Guanidinium Thiocyanate-Phenol-Chloroform Extraction" *Analytical Biochemistry*, 1987, pp. 156-159, vol. 162.

Conradt, H. et al. "Structure of the Carbohydrate Moiety of Human Interferon-β Secreted by a Recombinant Chinese Hamster Ovary Cell Line" *Journal of Biological Chemistry*, Oct. 25, 1987, pp. 14600-14605, vol. 262, No. 30.

Costello, C. "Time, Life . . . and Mass Spectrometry New Techniques to Address Biological Questions" *Biophysical Chemistry*, 1997, pp. 173-188, vol. 68.

Cummings, R. D. "Structure and Function of the Selectin Ligand PSGL-1" *Brazilian Journal of Medical and Biological Research*, 1999, pp. 519-528, vol. 32, No. 5.

Dell, A. et al. "Glycoprotein Structure Determination by Mass Spectrometry" *Science*, Mar. 23, 2001, pp. 2351-2356, vol. 291.

Derynck, R. et al. "Isolation and Structure of a Human Fibroblast Interferon Gene" *Nature*, Jun. 19, 1980, pp. 542-547, vol. 285.

Devereux, J. et al. "A comprehensive set of sequence analysis programs for the VAX" *Nucleic Acids Research*, 1984, pp. 387-395, vol. 12, No. 1.

Domon, B. et al. "Structure Elucidation of Glycosphingolipids and Gangliosides Using High-Performance Tandem Mass Spectrometry" *Biochemistry*, 1988, pp. 1534-1543, vol. 27.

Fenn, J. et al. "Electrospray Ionization for Mass Spectrometry of Large Biomolecules" *Science*, Oct. 6, 1989, pp. 64-71, vol. 246.

Graham, F. L. et al. "A New Technique for the Assay of Infectivity of Human Adenovirus 5 DNA" *Virology*, 1973, pp. 456-467, vol. 52.

Grantham, R. "Amino Acid Difference Formula to Help Explain Protein Evolution" *Science*, Sep. 6, 1974, pp. 862-864, vol. 185, No. 4154.

Gray, G. "Linkage Analysis Using Reductive Cleavage Method" *Methods in Enzymology*, 1990, pp. 573-587, vol. 193.

Harvey, D. J. "Collision-Induced Fragmentation of Underivatized N-Linked Carbohydrates Ionized by Electrospray" *Journal of Mass Spectrometry*, 2000, pp. 1178-1190, vol. 35.

Hillenkamp, F. et al. "Matrix-Assisted Laser Desorption/Ionization Mass Spectrometry of Biopolymers" *Analytical Chemistry*, Dec. 15, 1991, pp. 1193-1203, vol. 63, No. 24.

Innis, M. et al. "Procedures for Expression, Modification, and Analysis of Human Fibroblast Interferon (IFN-β) Genes in Heterologous Cells" *Methods in Enzymology*, 1986, pp. 397-403, vol. 119.

Kagawa, Y. et al. "Comparative Study of the Asparagine-Linked Sugar Chains of Natural Human Interferon-β1 and Recombinant Human Interferon-β1 Produced by Three Different Mammalian Cells" *Journal of Biological Chemistry*, Nov. 25, 1988, pp. 17508-17515, vol. 263, No. 33.

Kao, F. et al. "Genetics of Somatic Mammalian Cells, VII. Induction and Isolation of Nutritional Mutants in Chinese Hamster Cells" *Proc N.A.S.*, 1968, pp. 1275-1281, vol. 60.

Kaufman, R. et al. "Amplification and Expression of Sequences Cotransfected with a Modular Dihydrofolate Reductase Complementary DNA Gene" *J. Mol. Biol.*, 1982, pp. 601-621, vol. 159.

Martinez, G. et al. "Protein Salting-Out Method Applied to Genomic DNA Isolation from Fish Whole Blood" *BioTechniques*, Feb. 1998, pp. 238-239, vol. 24, No. 2.

Miyaji, H. et al. "Efficient Expression of Human Beta-Interferon in Namalwa KJM-1 Cells Adapted to Serum-Free Medium by a DHFR Gene Coamplification Method" *Cytotechology*, 1990, pp. 173-180, vol. 4.

Morris, H. et al. "Fab-Mapping of Recombinant-DNA Protein Products" *Biochemical and Biophysical Research Communications*, Nov. 30, 1983, pp. 299-305, vol. 117 No. 1.

Mory, Y et al. "Synthesis of Human Interferon β$_1$ in *Escherichia coli* Infected by a Lambda Phage Recombinant Containing a Human Genomic Fragment" *Eur. J. Biochem.*, 1981, pp. 197-202, vol. 120.

Puck, T. et al. "Genetics of Somatic Mammalian Cells, III. Long-Term Cultivation of Euploid Cells From Human and Animal Subjects" *The Journal of Experimental Medicine*, Jul. 24, 1958, pp. 945-959, vol. 108.

Reiser, W. et al. "Recombinant Human Interferon Beta From Mammalian Cell Lines" *Drug Res.*, 1987, pp. 482-485, vol. 37, No. 4.

Runkel, L. et al. "Structural and Functional Differences Between Glycosylated and Non-Glycosylated Forms of Human Interferon-β (IFN-β)" *Pharmaceutical Research*, 1998, pp. 641-649, vol. 15, No. 4.

Smith, T. F. et al. "Identification of Common Molecular Subsequences" *J. Mol. Biol.*, 1981, pp. 195-197, vol. 147.

Smith, T. F. et al. "Comparison of Biosequences" *Advances in Applied Mathematics*, 1981, pp. 482-489, vol. 2.

Tarentino, A. et al. "Deglycosylation of Asparagine-Linked Glycans by Peptide: N-Glycosidase F" *Biochemistry*, 1985, pp. 4665-4671, vol. 24, No. 17.

(56) References Cited

OTHER PUBLICATIONS

Urlaub, G. et al. "Isolation of Chinese Hamster Cell Mutants Deficient in Dihydrofolate Reductase Activity" *Proc. Natl. Acad. Sci. USA*, Jul. 1980, pp. 4216-4220, vol. 77, No. 7.
Wilm, M. et al. "Analytical Properties of the Nanoelectrospray Ion Source" *Anal. Chem.*, Jan. 1, 1996, pp. 1-8, vol. 68, No. 1.
Yousefi, S. et al. "A Practical Cytopathic Effect/Dye-Uptake Interferon Assay for Routine Use in the Clinical Laboratory" *Brief Scientific Reports*, Jun. 1985, pp. 735-740, vol. 83, No. 6.
Office Action mailed Mar. 18, 2009 in U.S. Appl. No. 10/581,172, filed Feb. 6, 2007.
Tikhomirov, M.M. et al. "High-Performance Liquid Chromatographic Investigation of the Amino Acid, Amino Sugar and Neutral Sugar Content in Glycoproteins", *Journal of Chromatography*, 1978, pp. 197-203, vol. 167.
Armour, K. L. et al. "Recombinant human IgG molecules lacking Fcγ receptor I binding and monocyte triggering activities" *Eur. J. Immunol.*, 1999, pp. 2613-2624, vol. 29.
Bodmer, J.-L. et al. "The molecular architecture of the TNF superfamily" *Trends in Biochemical Sciences*, Jan. 2002, pp. 19-26, vol. 27, No. 1.
Bossen, C. et al. "Interactions of Tumor Necrosis Factor (TNF) and TNF Receptor Family Members in the Mouse and Human" *The Journal of Biological Chemistry*, May 19, 2006, pp. 13964-13971, vol. 281, No. 20.
Carter, P. J. "Potent antibody therapeutics by design" *Nature*, May 2006, pp. 343-357, vol. 6.
Hinton, P. R. et al. "Engineered Human IgG Antibodies with Longer Serum Half-lives in Primates" *The Journal of Biological Chemistry*, Feb. 20, 2004, pp. 6213-6216, vol. 279, No. 8.
Idusogie, E. E. et al. "Mapping of the C1q Binding Site on Rituxan, a Chimeric Antibody with a Human IgG1 Fc" *The Journal of Immunology*, 2000, pp. 4178-4184, vol. 164.
Idusogie, E. E. et al. "Engineered Antibodies with Increased Activity to Recruit Complement" *The Journal of Immunology*, 2001, pp. 2571-2575, vol. 166.
Knight, E. et al. "Human Fibroblast Interferon" *The Journal of Biological Chemistry*, Apr. 25, 1981, pp. 3609-3611, vol. 256, No. 8.
Locksley, R. M. et al. "The TNF and TNF Receptor Superfamilies: Integrating Mammalian Biology" *Cell*, Feb. 23, 2001, pp. 487-501, vol. 104.
Moore, P. A. et al. "BLyS: Member of the Tumor Necrosis Factor Family and B Lymphocyte Stimulator" *Science*, Jul. 9, 1999, pp. 260-263, vol. 285.
Novak, A. J. et al. "Expression of BCMA, TACI, and BAFF-R in multiple myeloma: a mechanism for growth and survival" *Blood*, 2004, pp. 689-694, vol. 103.
Shields, R. L. et al. "High Resolution Mapping of the Binding Site on Human IgG1 for FcγR1, FcγRII, FcγRIII, and FcRn and Design of IgG1 Variants with Improved Binding to the FcγR" *The Journal of Biological Chemistry*, Mar. 2, 2001, pp. 6591-6604, vol. 276, No. 9.
Steurer, W. et al. "Ex Vivo Coating of Islet Cell Allografts with Murine CTLA4/Fc Promotes Graft Tolerance" *The Journal of Immunology*, 1995, pp. 1165-1174, vol. 155.
Vaccaro, C. et al. "Engineering the Fc region of immunoglobulin G to modulate in vivo antibody levels" *Nature Biotechnology*, Oct. 2005, pp. 1283-1288, vol. 23, No. 10.
Vlatakis, G. et al. "Dye-Ligand Chromatography for the Resolution and Purification of Restriction Endonucleases" *Applied Biochemistry and Biotechnology*, 1987, pp. 201-212, vol. 15.
Written Opinion in International Application No. PCT/EP2008/064208, Dec. 15, 2009, pp. 1-7.
Denizli, A. et al. "Dye-ligand affinity systems" *J. Biochem. Biophys. Methods*, 2001, pp. 391-416, vol. 49, XP-002466734.
Gross, J. A. et al. "TACI and BCMA are receptors for a TNF homologue implicated in B-cell autoimmune disease" *Nature*, Apr. 27, 2000, pp. 995-999, vol. 404.
Hahne, M. et al. "APRIL, a New Ligand of the Tumor Necrosis Factor Family, Stimulates Tumor Cell Growth" *J. Exp. Med.*, Sep. 21, 1998, pp. 1185-1190, vol. 188, No. 6.
Hymowitz, S. G. et al. "Structures of APRIL-Receptor Complexes: Like BCMA, TACI employs only a single cysteine-rich domain for High Affinity Ligand Binding" *The Journal of Biological Chemistry*, Feb. 25, 2005, pp. 7218-7227, vol. 28, No. 8.
Melchers, F. "Actions of BAFF in B cell maturation and its effects on the development of autoimmune disease" *Ann. Rheum. Dis.*, 2003, pp. 25-27, vol. 62.
Subramanian, S. "Dye-Ligand Affinity Chromatography: The Interaction of Cibacron Blue F3GA With Proteins and Enzymes" *Critical Reviews in Biochemistry*, 1984, pp. 169-205, vol. 16, Issue 2, XP-000646812.
Naismith, J. H. et al. "Modularity in the TNF-receptor family" *TIBS*, Feb. 1998, pp. 74-79, vol. 23.
Von Bulow, G.-U. et al. "NF-AT Activation Induced by a CAML-Interacting Member of the Tumor Necrosis Factor Receptor Superfamily" *Science*, Oct. 3, 1997, pp. 138-141, vol. 278.
Emlen, W. "Purification of DNA Antibodies Using Cibacron Blue F3GA Affinity Chromatogrphy" *Journal of Immunological Methods*, 1983, pp. 205-215, vol. 62, XP-002466735.
Xia, X.-Z. et al. "TACI Is a TRAF-interacting Receptor for TALL-1, a Tumor Necrosis Factor Family Member Involved in B Cell Regulation" *J. Exp. Med.*, Jul. 3, 2000, pp. 137-143, vol. 192, No. 1.
Written Opinion in International Application No. PCT/EP2008/064210, Jan. 13, 2009, pp. 1-8.
Bell, J. et al. "Blue Dextran: Influence on Chromatographic Profile and Immunoreactivity of Human Follicle-Stimulating Hormane (HFSH) (38852)" *Proc. Soc. Exp. Biol. Med.*, 1975, pp. 565-569, vol. 149.
Nomura, K. et al. "Partial purification and characterization of a renotropic fraction from ovine pituitaries" *Proc. Natl. Acad. Sci. USA*, Nov. 1982, pp. 6675-6679, vol. 79.
El Rassi, Z., Handbook of HPLC—Chromatographic Sciences Series, vol. 78, Edited by E. Katz, R. Eksteen, P. Schoenmakers and N. Miller, Marcel Dekker Inc., New York, USA, 1998, pp. 989 ISBN 0-8247-9444, pp. 463-482, Ch. 12, Hydrophobic Interaction Chromatography of Biopolymers.
Santi, D. V. et al. "Purification and Characterization of Recombinant *Pneumocystis carinii* Thymidylate Synthase" *Protein Expression and Purification*, 1991, pp. 350-354, vol. 2.
Soto, A. M. et al. "A Plasma-Borne Specific Inhibitor of the Proliferation of Human Estrogen-Sensitive Breast Tumor Cells (Estrocolyone-I)" *J. Steroid Biochem. Molec. Biol.*, 1992, pp. 703-712, vol. 43, No. 7.
"Source 15 HIC" [Online], Nov. 2002, pp. 2002-2011, *Amersham Biosciences*, XP002437160, Retrieved from the Internet.
Bradford, M.M. "A Rapid and Sensitive Method for the Quantitation of Microgram Quantities of Protein Utilizing the Principle of Protein-Dye Binding", *Analytical Biochemistry*, 1976, pp. 248-254, vol. 72.
Burgues, S. et al. "Subcutaneous self-administration of highly purified follicle stimulating hormone and human chorionic gonadotrophin for the treatment of male hypogonadotrophic hypogonadism", *Human Reproduction*, 1997, pp. 980-986, vol. 12, No. 5.
Chiba, K. et al. "Isolation and Partial Characterization of LH, FSH and TSH from Canine Pituitary Gland", *Endocrine Journal*, 1997, pp. 205-218, vol. 44, No. 2.
Dulley, J.R. et al. "A Simple Technique for Eliminating Interference by Detergents in the Lowry Method of Protein Determination", *Analytical Biochemistry*, 1975, pp. 136-141, vol. 64.
Hartree, E.F. "Determination of Protein: A Modification of the Lowry Method That Gives a Linear Photometric Response", *Analytical Biochemistry*, 1972, pp. 422-427, vol. 48.
Lowry, O.H. et al. "Protein Measurement with the Folin Phenol Reagent", *J. Biol. Chem.*, 1951, pp. 265-275, vol. 193.
Lynch, S.S. et al. "The Extraction and Purification of Human Pituitary Follicle-stimulating hormone and luteinizing hormone", *Acta Endocrinologica*, 1988, pp. 12-19, vol. 288.
Steelman, S.L. et al. "Assay of the Follicle Stimulating Hormone Based on the Augmentation with Human Chorionic Gonadotropin", *Endocrinology*, 1953, pp. 604-616, vol. 53.
Van Hell, H. et al. "Effects of Human Menopausal Gonadotrophin Preparations in Different Bioassay Methods", *Acta Endocrinologica*, 1964, pp. 409-418, vol. 47.

(56) References Cited

OTHER PUBLICATIONS

Flack, M. R. et al. "Site-directed Mutagenesis Defines the Individual Roles of the Glycosylation Sites on Follicle-stimulating Hormone" *The Journal of Biological Chemistry*, May 13, 1994, pp. 14015-14020, vol. 269, No. 19.

Na, H. K. et al. "Purification and Characterization of Recombinant Human Follicle Stimulating Hormone Produced by Chinese Hamster Ovary Cells" *Journal of Microbiology and Biotechnology*, 2005, pp. 395-402, vol. 15, No. 2.

Oki, S. et al. "Macrophage Migration Inhibitory Factor (MIF) Produced by a Human T Cell Hybridoma Clone" *Lymphokine and Cytokine Research*, 1991, pp. 273-280, vol. 10, No. 4.

Peyer, C. et al. "Purification and characterization of β-xylosidase from potatoes (*Solanum tuberosum*)" *BBA*, 2004, pp. 27-35, vol. 1672, No. 1, Elsevier Science Publishers.

Ribela, M. T. et al. "Synthesis and chromatographic purification of recombinant human pituitary hormones" *Journal of Chromatography B*, 2003, pp. 285-316, vol. 790, Nos. 1-2.

Miyaji, H. et al. "Expression of human beta-interferon in Namalwa KJM-1 which was adapted to serum-free medium" *Cytotechnology*, 1990, pp. 133-140, vol. 3.

Paty, D.W. et al. "Interferon beta-1b is effective in relapsing-remitting multiple sclerosis. II. MRI analysis results of a multicenter, randomized, double-blind, placebo-controlled trial" *Neurology*, 1993, pp. 662-667, vol. 43.

2002 ATCC Catalog No. 30-2001, p. 1.

Protein Purification Handbook, 18-1132-29, "Polishing" In Chapter 6 of Amersham Pharmacia Biotech AB, 1999, pp. 29-36.

* cited by examiner

Plasmid containing the human IFNß gene and the mouse DHFR gene

Transfection

DUKX-B11 (DHFR- CHO Cells)

Selection of DHFR+ transfectants in Thymidine free Medium

Screening of DHFR+ clones for IFN-b production

Gene amplification in culture medium containing MTX

Cloning and subcloning

Selection and initial characterization of high producer cell line

| STAGE | OPERATION |
|---|---|
| | ⇩ |
| I | Clarification |
| | ⇩ |
| II | Blue Sepharose 6 FF |
| | ⇩ |
| III | Ultrafiltration |
| | ⇩ |
| IV | CM Sepharose FF |
| | ⇩ |
| V | RP-HPLC |
| | ⇩ |
| VI | Ultrafiltration |
| | ⇩ |
| VII | SE chromatography |
| | ⇩ |
| VIII | Filtration |
| | ⇩ |
| | IFN-ß-1a bulk |

Fig. 2

| Species | Observed mass | Attribution | Expected ass |
|---|---|---|---|
| A | 21796 | P + 1 Fuc Biant | 21793 |
| B | 22088 | P + 1 Fuc Biant + 1SA | 22084 |
| B* | 22186 | P + 1 Fuc Biant + 1SA+phosphate adduct | 22182 |
| C | 22380 | P + 1 Fuc Biant + 2SA | 22375 |
| C* | 22478 | P + 1 Fuc Biant + 2SA+phosphate adduct | 22473 |
| → | 22526 | P + 2 Fuc Biant + 2SA | 22521 |
| ⇢ | 22672 | P + 3 Fuc Biant + 2SA | 22667 |
| D | 22746 | P + 1 Fuc Triant (or Fuc Baint with a lactosamine repeat) + 2SA | 22739 |
| E | 23036 | P + 1 Fuc Triant + 3SA | 23031 |
| F | 23390 | P + 1 Fuc Tetrant (or Fuc Triant with a lactosamine repeat) + 2 SA | 23400 |

Fig. 5 A Major oligosaccharides

I)

II)

Fig. 5 B Minor oligosaccharides

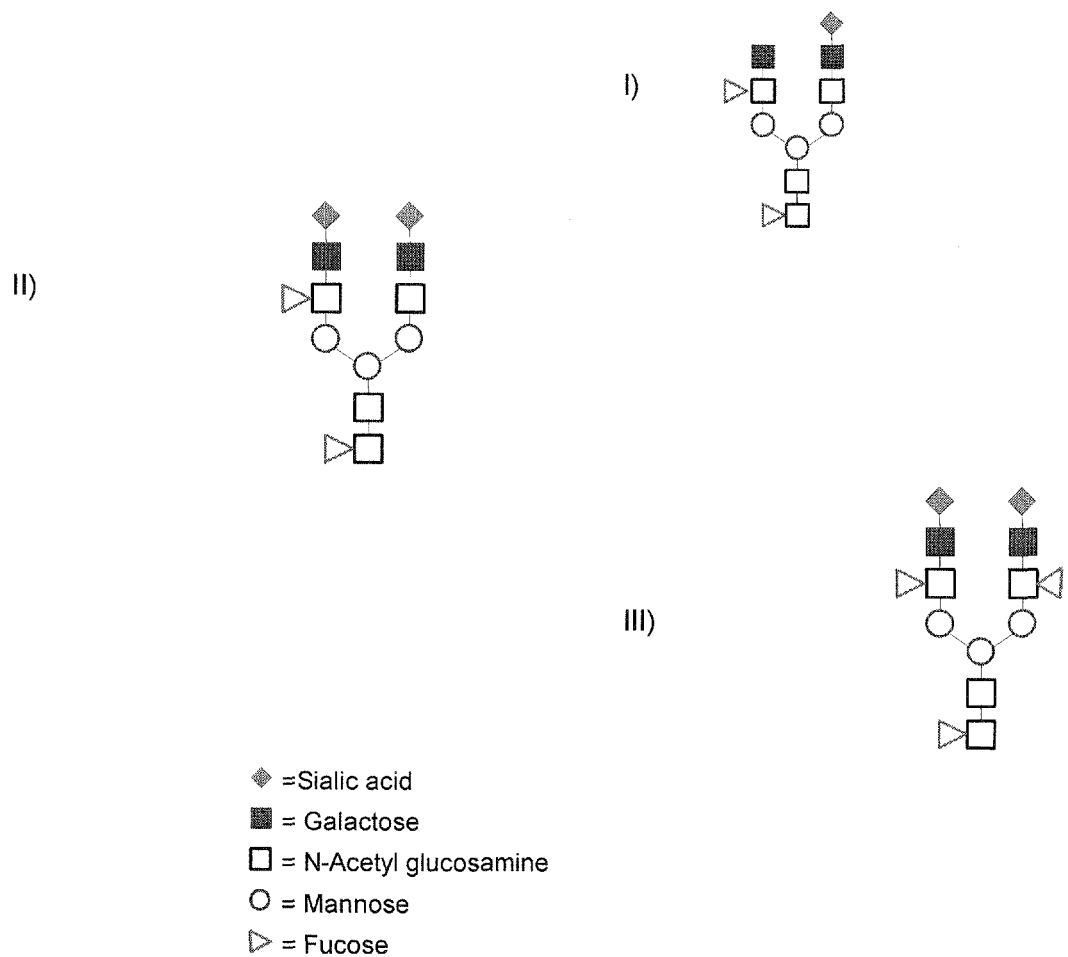
Fig. 5 C Minor oligosaccharides with two or three Fucoses
◆ = Sialic acid
■ = Galactose
□ = N-Acetyl glucosamine
○ = Mannose
▷ = Fucose

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
cctcggcctc tgagctattc                                                   20

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
cacaaataaa gcatttttt                                                    20

<210> SEQ ID NO 3
<211> LENGTH: 22
<212> TYPE: DNA
<213> ORGANISM: artificial sequence
<220> FEATURE:
<223> OTHER INFORMATION: primer

<400> SEQUENCE: 3
atgaccaaca agtgtctcct cc                                                22

<210> SEQ ID NO 4
<211> LENGTH: 22
<212> TYPE: DNA
<213> ORGANISM: artificial sequence
<220> FEATURE:
<223> OTHER INFORMATION: primer

<400> SEQUENCE: 4
acttacaggt tacctccgaa ac                                                22
```

PROCESS FOR THE PREPARATION OF GLYCOSYLATED INTERFERON BETA

CROSS-REFERENCE TO RELATED APPLICATIONS

This application is a divisional of U.S. application Ser. No. 12/064,422, filed Feb. 21, 2008, which is the U.S. national stage application of International Patent Application No. PCT/EP2005/054220, filed Aug. 26, 2005, the disclosures of which are hereby incorporated by reference in their entireties, including all figures, tables and amino acid or nucleic acid sequences.

FIELD OF THE INVENTION

The present invention relates to processes for producing recombinant human interferon beta under serum-free culture conditions, processes of purifying recombinant human interferon beta and to an interferon beta protein having a unique glycosylation pattern.

BACKGROUND OF THE INVENTION

Proteins have become commercially important as drugs that are also generally called "biologicals". One of the greatest challenges is the development of cost effective and efficient processes for the production of recombinant proteins on a commercial scale.

The biotech industry makes an extensive use of mammalian cells for the manufacturing of recombinant glycoproteins for human therapy.

Suitable cells that are widely used for production of polypeptides turned out to be Chinese Hamster Ovary (CHO) cells.

CHO cells were first cultured by Puck (1958) from a biopsy of an ovary from a female Chinese hamster. From these original cells a number of sub-lines were prepared with various characteristics. One of these CHO cell lines, CHO-K1, is proline-requiring and is diploid for the dihydrofolate reductase (DHFR) gene. Another cell line derived from this cell line is a DHFR deficient CHO cell line (CHO DUK B11) (PNAS 77, 1980, 4216-4220), which is characterized by the loss of DHFR function as a consequence of a mutation in one DHFR gene and the subsequent loss of the other gene.

Further cells that are frequently used for the production of proteins intended for administration to humans are human cell lines such as the human fibrosarcoma cell line HT1080 or the human embryonic kidney cell line 293, a human embryonic retinoblast-derived cell line such as e.g. PER.C6, an amniotic cell derived-cell line or a neuronal-derived cell line.

Cells from a suitable cell line are stably transfected with an expression vector comprising the coding sequence of the protein of interest to be produced, together with regulatory sequences such as promoters, enhancers, or polyA signals that ensure stable and correct expression of the protein of interest. Further genes usually present on expression vectors are marker genes such as e.g. positive selections markers (e.g. neo gene) that select the stably transfected cells from the untransfected and transiently transfected cells. Amplifiable genes such as the DHFR gene are used for amplification of the coding sequences.

Once a clone expressing the protein of interest has been established, a manufacturing process starting from this clone must be established allowing for production in high amounts and such a quality as is required for proteins destined for human administration.

Such manufacturing processes are generally carried out in bioreactors. There are different modes of operation. Today, fed-batch and perfusion cultures are the two dominant modes of industrial operation for the mammalian cell culture processes that require large amount of proteins (Hu and Aunins 1997). Whatever the production technology of choice is, development efforts aim at obtaining production processes that warrant high volumetric productivity, batch-to-batch consistency, homogenous product quality at low costs.

The decision between fed-batch or perfusion production mode is mainly dictated by the biology of the clone and the property of the product, and is done on a case-by-case basis during the course of the development of a new drug product (Kadouri and Spier 1997).

When the selection is a perfusion process, one of the culture systems of choice is stationary packed-bed bioreactor in which cells are immobilized onto solid carriers. This system is easy to operate and with appropriate carriers and culture conditions very high cell density (of ~$10^7$-$10^8$ cell·ml$^{-1}$) can be achieved.

A consequence of this high cell density is the need for an intensive medium perfusion rate (feed and harvest) that should be used in order to keep the cells viable and productive. It appears that the perfusion rate is one of the central parameters of such a process: it drives the volumetric protein productivity, the protein product quality and has a very strong impact on the overall economics of the process.

For the cell culture process, in the past culture media were supplemented with serum, which serves as a universal nutrient for the growth and maintenance of all mammalian cell lines that produce biologically active products. Serum contains hormones, growth factors, carrier proteins, attachment and spreading factors, nutrients, trace elements, etc. Culture media usually contained up to about 10% of animal serum, such as fetal bovine serum (FBS), also called fetal calf serum (FCS).

Although widely used, serum has many limitations. It contains high levels of numerous proteins interfering with the limited quantities of the desired protein of interest produced by the cells. These proteins derived from the serum must be separated from the product during downstream processing such as purification of the protein of interest, which complicates the process and increases the cost.

The advent of BSE (Bovine Spongiform Encephalopathy), a transmissible neurodegenerative disease of cattle with a long latency or incubation period, has raised regulatory concerns about using animal-derived sera in the production of biologically active products.

There is therefore a great demand for the development of alternative cell culture media free from animal sources that support cell growth and maintain cells during the production of biologically active products.

Generally, cell culture media comprise many components of different categories, such as amino acids, vitamins, salts, fatty acids, and further compounds:

Amino acids: For instance, U.S. Pat. No. 6,048,728 (Inlow et al.) discloses that the following amino acids may be used in a cell culture medium: Alanine, Arginine, Aspartic Acid, Cysteine, Glutamic Acid, Glutamin, Glycine, Histidine, Isoleucine, Leucine, Lysine, Methionine, Phenylalanine, Proline, Serine, Tryptophan, Tyrosine, Threonine, and Valine.

Vitamins: US 2003/0096414 (Ciccarone et al.) or U.S. Pat. No. 5,811,299 (Renner et al.) for example describe that the following vitamins may be used in a cell culture medium: Biotin, Pantothenate, Choline Chloride, Folic Acid, Myo-Inositol, Niacinamide, Pyridoxine, Riboflavin, Vitamin B12, Thiamine, Putrescine.

Salts: For instance, U.S. Pat. No. 6,399,381 (Blum et al.) discloses a medium comprising $CaCl_2$, KCl, $MgCl_2$, NaCl, Sodium Phosphate Monobasic, Sodium Phosphate Dibasic, Sodium Selenite, $CuSO_4$, $ZnCl_2$. Another example for a document disclosing the inorganic salts that may be used in a culture medium is US 2003/0153042 (Arnold et al.), describing a medium comprising $CaCl_2$, KCl, $MgCl_2$, NaCl, Sodium Phosphate Monobasic, Sodium Phosphate Dibasic, $CuCl_2.2H_2O$, $ZnCl_2$.

Fatty acids: Fatty acids that are known to be used in media are Arachidonic Acid, Linoleic Acid, Oleic Acid, Lauric Acid, Myristic Acid, as well as Methyl-beta-Cyclodextrin, see e.g. U.S. Pat. No. 5,045,468 (Darter). It should be noted that cyclodextrin is not a lipid per se, but has the ability to form a complex with lipids and is thus used to solubilize lipids in the cell culture medium.

Further components, in particular used in the frame of serum-free cell culture media, are compounds such as glucose, glutamine, Na-pyruvate, insulin or ethanolamine (e.g. EP 274 445), or a protective agent such as Pluronic F68. Pluronic® F68 (also known as Poloxamer 188) is a block copolymer of ethylene oxide (EO) and propylene oxide (PO).

Standard "basic media" are also known to the person skilled in the art. These media already contain several of the medium components mentioned above. Examples of such media that are widely applied are Dulbecco's Modified Eagle's Medium (DMEM), Roswell Park Memorial Institute Medium (RPMI), or Ham's medium.

After production of the protein of interest in the bioreactor, the protein of interest needs to be purified from the cell culture harvest. The cell culture harvest may e.g. be cell extracts for intracellular proteins, or cell culture supernatant for secreted proteins.

While many methods are now available for large-scale preparation of proteins, crude products, such as cell culture harvest, contain not only the desired product but also impurities which are difficult to separate from the desired product.

The health authorities request high standards of purity for proteins intended for human administration. As a further difficulty, many purification methods may contain steps requiring application of low or high pH, high salt concentrations or other extreme conditions that may jeopardize the biological activity of a given protein. Thus, for any protein it is a challenge to establish a purification process allowing for sufficient purity while retaining the biological activity of the protein.

Ion exchange chromatographic systems have been used widely for separation of proteins primarily on the basis of differences in charge. In ion exchange chromatography, charged patches on the surface of the solute are attracted by opposite charges attached to a chromatography matrix, provided the ionic strength of the surrounding buffer is low. Elution is generally achieved by increasing the ionic strength (i.e. conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution). Resins that may be used in ion exchange chromatography may contain different functional groups: diethylaminoethyl (DEAE) or diethyl-(2-hydroxy-propyl)aminoethyl (QAE) have chloride as counter ion, while carboxymethyl (CM) and sulphopropyl (SP) have sodium as counter ion, for example.

Chromatographic systems having a hydrophobic stationary phase offer an alternative basis for separations and have also been widely employed in the purification of proteins. Included in this category are hydrophobic interaction chromatography (HIC) and reversed phase liquid chromatography (RPLC). The physicochemical basis for separation by HIC and RPLC is the hydrophobic effect, proteins are separated on a hydrophobic stationary phase based on differences in hydrophobicity.

Reverse phase chromatography is a protein purification method closely related to HIC, as both are based upon interactions between solvent-accessible non-polar groups on the surface of biomolecules and hydrophobic ligands of the matrix. However, ligands used in reverse phase chromatography are more highly substituted with hydrophobic ligands than HIC ligands. While the degree of substitution of HIC adsorbents may be in the range of 10-50 µmoles/mL of matrix of C2-C8 aryl ligands, several hundred µmoles/mL of matrix of C4-C8 alkyl ligands are usually used for reverse phase chromatography adsorbents.

The Source 30RPC column is a polymeric reverse phase matrix. It is based on rigid, monosized 30 micron diameter polystyrene/divinyl benzene beads. Its characteristics can be summarized as follows: Exceptionally wide pH range (1-12), high selectivity, high chemical resistance, high capacity and high resolution at high flow rates.

Size-exclusion chromatography (SEC), also called gel-permeation chromatography (GPC), uses porous particles to separate molecules of different sizes. It is generally used to separate biological molecules and to determine molecular weights and molecular weight distributions of polymers. Molecules that are smaller than the pore size can enter the particles and therefore have a longer path and longer transit time than larger molecules that cannot enter the particles. All molecules larger than the pore size are not retained and elute together. Molecules that can enter the pores will have an average residence time in the particles that depends on the molecules size and shape. Different molecules therefore have different total transit times through the column.

Blue Sepharose is a chromatography resin based on a dye-ligand affinity matrix. The ligand, Cibacron Blue F3G-A, is covalently coupled to Sepharose™ through chlorotriazine ring (Clonis et al., 1987).

Blue Sepharose has been used for the purification of interferon beta (Mory et al., 1981).

Interferon beta (interferon-β or IFN-β) is a naturally occurring soluble glycoprotein belonging to the class of cytokines. Interferons (IFNs) have a wide range of biological activities, such as anti-viral, anti-proliferative and immunomodulatory properties.

The three major interferons are referred to as IFN-alpha, IFN-beta and IFN-gamma. These interferons were initially classified according to their cells of origin (leukocytes, fibroblasts or T-cells). However, it became clear that several types might be produced by one cell. Hence leukocyte interferon is now called IFN-alpha, fibroblast interferon is IFN-beta, and T-cell interferon is IFN-gamma. There is also a fourth type of interferon, lymphoblastoid IFN, produced in the "Namalwa" cell line (derived from Burkitt's lymphoma), which seems to produce a mixture of both leukocyte and fibroblast IFN.

Human fibroblast interferon (IFN-beta) has antiviral activity and is also known to inhibit proliferation of cells. It is a polypeptide of about 20,000 Da induced by viruses and double-stranded RNAs. From the nucleotide sequence of the gene for fibroblast interferon, cloned by recombinant DNA technology, Derynck et al., 1980 deduced the complete amino acid sequence of the protein, which is 166 amino acid long.

Interferon-β has also been cloned. U.S. Pat. No. 5,326,859 describes the DNA sequence of human IFN-β and a plasmid for its recombinant expression in bacteria such as E. coli. European Patent No. 0 287 075 describes a CHO (Chinese Hamster Ovary) cell line, transfected with the interferon-β coding sequence and capable of producing recombinant interferon-β. The protein is described as being glycosylated with a biantennary (two branched) oligosaccharide, featuring a single fucose moiety.

Interferon beta has been expressed in several cell lines, such as CHO cells, BHK 21 (baby hamster kidney cells) and LTK (mouse L-thymidine kinase negative) cells (Reiser and Hauser, 1987). DHFR negative CHO cells have also been used for the expression of interferon beta (Innis and McCormick, 1982), (Chernajovsky et al., 1984).

Interferons are known to be glycosylated, often with different glycoforms. For example, the saccharide structure of IFN-β was shown to include a bi-antennary structure, featuring a single fucose saccharide and terminal galactose sialylation (Conradt et al., 1987). Glycosylation was shown to also be important for solubility, since the IFN-β precipitated after deglycosylation with glycopeptidase F. In addition, IFN-β produced by E. coli showed folding problems, due to lack of glycosylation in the bacterial expression system.

European Patent No. 0 529 300 describes a recombinant interferon-β having a specific glycosylation pattern, namely glycosylation with carbohydrate structures that feature one fucose per oligosaccharide unit. These carbohydrate structures are biantennary, triantennary and tetraantennary (two, three and four branched, respectively) oligosaccharides.

PCT Application No. WO 99/15193 also describes glycosylation of recombinant interferon-β featuring biantennary, triantennary and tetraantennary oligosaccharides. The constituent monosaccharides included mannose, fucose, N-acetylglucosamine, galactose and sialic acid.

Various studies have demonstrated the importance of glycosylation for stability. For example, non-glycosylated forms of recombinant interferon-β were shown to have significantly lower stability and also lower biological activity (Runkel et al., 1998).

Other studies have shown that recombinant and natural human interferon-β proteins have different glycosylation patterns (Kagawa et al., 1988).

Interferon beta is used as a therapeutic protein drug, a so-called biological, in a number of diseases, such as e.g. multiple sclerosis, cancer, or viral diseases such as e.g. SARS or hepatitis C virus infections.

Therefore, there is a need for processes for the efficient production and purification of interferon beta, and of cells expressing interferon beta in high amounts.

SUMMARY OF THE PRESENT INVENTION

The present invention is based on the development of a process for producing recombinant human interferon beta in a serum free medium.

Therefore, in a first aspect, the invention relates to a process for the manufacturing of glycosylated recombinant, preferably human interferon-β, comprising a step of culturing an interferon-β producing cell in a serum-free medium, the serum-free medium comprising:

about 10 to about 30 mM HEPES, preferably 20 mM of HEPES;

about 0.5 to about 3 mM Proline, preferably about 1 mM of Proline; and about 5500 to about 7000 mg/L sodium chloride, preferably about 6100 mg/L sodium chloride.

The present invention is further based on the development of a process for purifying recombinant interferon beta from a fluid, in particular from the cell culture harvest derived from cells producing interferon beta.

Therefore, in a second aspect, the invention relates to a process for the purification of recombinant human interferon from a fluid, comprising the steps of:

Subjecting the fluid to affinity chromatography;

Subjecting the eluate of the affinity chromatography to cation exchange chromatography;

Subjecting the eluate of the cation exchange chromatography to hydrophobic chromatography by RP-HPLC.

Analysis of the interferon beta produced by the process of the invention revealed that it is a composition of differentially glycosylated interferon beta, i.e. an interferon beta having a unique glycosylation pattern or profile. Therefore, in a third aspect, the invention relates to an interferon beta composition comprising an oligosaccharide structure comprising two or three fucose saccharides.

Uses of the recombinant human interferon-β produced according to the processes of the invention, in the manufacture of a medicament for the treatment of tumors, multiple sclerosis, viral infections, and uses of the serum-free cell culture medium of the invention for the production of interferon beta, are further aspects of the present invention.

BRIEF DESCRIPTION OF THE DRAWINGS

FIG. 2 shows a flowchart of the new purification process of IFN-β-1a.

FIG. 4 shows the ES-MS transformed spectrum of IFN-β-1a obtained by the new process wherein:

P=protein (IFN-β);

Fuc Biant=fucosylated biantennary complex type oligosaccharide;

Fuc Triant=fucosylated triantennary complex type oligosaccharide;

Fuc Tetrant=fucosylated tetrantennary complex type oligosaccharide;

SA=sialic acid.

Figure 5:
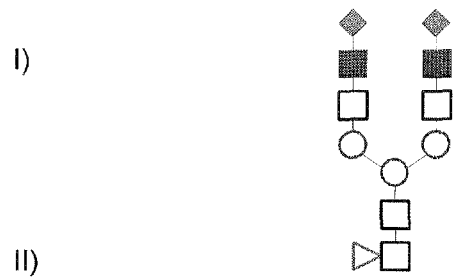
Figure 5:
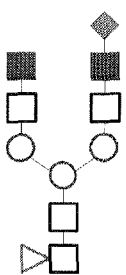
Figure 5:
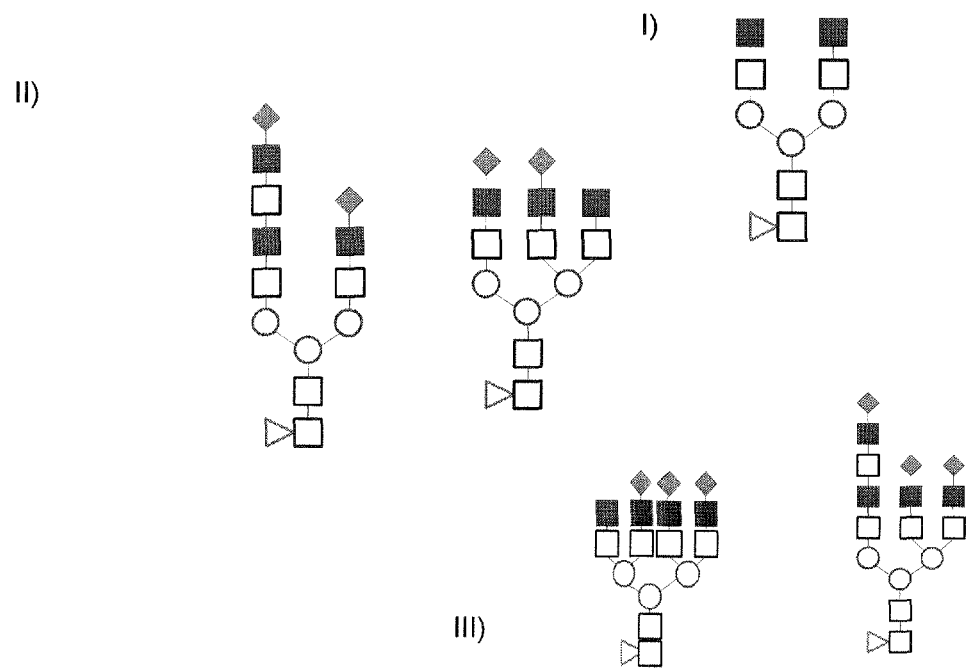

FIG. 5 shows oligosaccharide structures in IFN-β-1a; wherein:

FIG. 5 A shows the major oligosaccharides:
  I. Disialylated biantennary ($NeuAc_2.Hex_5.HexNAc_4.Fuc$)
  II. Monosialyl biantennary ($NeuAc.Hex_5.HexNAc_4.Fuc$)

FIG. 5 B shows the minor oligosaccharides, wherein:
  I. Non sialylated biantennary ($Hex_5.HexNAc_4.Fuc$)
  II. Mono and Disialylated triantennary structure or disialylated biantennary with N-acetyl lactosamine repeat structure ($NeuAc_2.Hex_6.HexNAc_5.Fuc$)
  III. Trisialylated triantennary with N-acetyl lactosamine repeat structure or Trisialylated tetrantennary structure ($NeuAc_3.Hex_7.HexNAc_6.Fuc$)

FIG. 5 C shows the minor oligosaccharides with two or three Fucose residues:

I. Monosialyl biantennary structure with two Fucose (NeuAc.Hex$_5$.HexNAc$_4$.Fuc$_2$)
II. Disialylated biantennary structure with two Fucose (NeuAc$_2$.Hex$_5$.HexNAc$_4$.Fuc$_2$)
III. Disialylated biantennary structure with three Fucose (NeuAc$_2$.Hex$_5$.HexNAc$_4$.Fuc$_3$)

Figure 6:
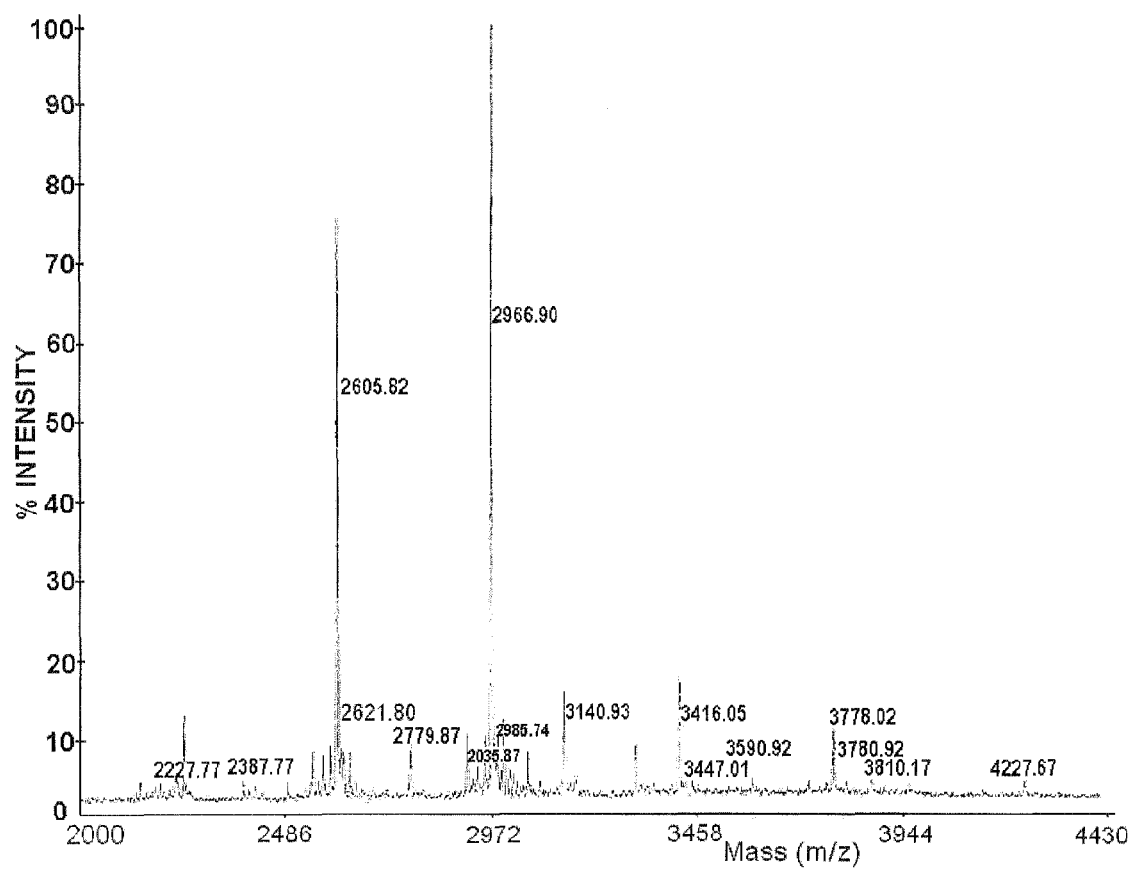

FIG. 6 shows the MALDI spectrum of the new IFN-β-1a with permethylated glycans.

DETAILED DESCRIPTION OF THE INVENTION

The first aspect of the present invention is based on the development of a process for the production of interferon beta under serum-free cell culture conditions. In accordance with the present invention, the process for the manufacturing of glycosylated recombinant interferon beta comprises a step of culturing an interferon beta producing cell in a serum-free medium, the serum-free medium comprising:
about 10 to about 30 mM HEPES, preferably 20 mM of HEPES;
about 0.5 to about 3 mM proline, preferably about 1 mM of proline; and
about 5500 to about 7000 mg/l sodium chloride, preferably about 6100 mg/l sodium chloride.

The serum-free medium may e.g. comprise 9, 10, 11, 12, 13, 14, 15, 16, 17, 18, 19, 20 or 21 mM of HEPES (2-(4-(2-HYDROXYETHYL)-1-PIPERAZINYL)ETHANE-SULFONIC ACID) buffer. It may also e.g. comprise 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3,1 mM of Proline.

Sodium chloride concentrations in the serum-free medium of the invention may e.g. be about 5400, 5500, 5600, 5700, 5800, 5900, 6000, 6100, 6200, 6300, 6400, 6500, 6600, 6700, 6800, 6900, 7000, 7100 mg/L.

In a preferred embodiment, the serum-free medium further comprises about 10 to about 20, preferably about 15 mg/L Phenol Red. The Phenol Red concentration may e.g. be 9, 10, 11, 12, 13, 14, 15, 16, 17, 18, 19, 20, 21 mg/L.

In the frame of the process of the present invention, the above-identified components may be used in any suitable known serum-free medium. Examples of such serum-free media are listed below:

| Medium | Manufacturer | Cat. No. |
|---|---|---|
| EX-CELL 302 | JRH | 14312-1000M |
| EX-CELL 325 | JRH | 14335-1000M |
| CHO-CD3 | Sigma | C-1490 |
| CHO III PFM | Gibco | 96-0334SA |
| CHO-S-SFM II | Gibco | 12052-098 |
| CHO-DHFR | Sigma | C-8862 |
| ProCHO 5 | Cambrex | BE12-766Q |
| SFM4CHO | HyClone | SH30549.01 |
| Ultra CHO | Cambrex | 12-724Q |
| HyQ PF CHO | HyClone | SH30220.01 |
| HyQ SFX CHO | HyClone | SH30187.01 |
| HyQ CDM4CHO | HyClone | SH30558.01 |
| IS CHO-CD | Irvine Scientific | #91119 |
| IS CHO-V | Irvine Scientific | #9197 |

The interferon beta producing cell that may be cultured in accordance with the present invention may be any mammalian cell, including animal or human cells, such as e.g. 3T3 cells, COS cells, human osteosarcoma cells, MRC-5 cells, BHK cells, VERO cells, CHO cells, CHO-S cells, HEK 293 cells, HEK 293 cells, Normal Human fibroblast cells, Stroma cells, Hepatocytes cells and PER.C6 cells that has been modified to express, and preferably secrete interferon beta.

The cell to be used in the process of the invention is preferably an interferon beta expressing CHO clone such as e.g. the cell line described by Reiser and Hauser (1987) or the cells described by Innis and McCormick (1982).

The term "interferon beta", as used herein, is also called IFN beta, or IFN-β, and encompasses interferon beta derived from any species and preferably human interferon beta, a 166 amino acid glycoprotein with a molecular weight of approximately 22,500 daltons. The term "interferon beta", as used herein, also encompasses functional derivatives, muteins, analogs, or fragments of IFN-beta. The term "interferon beta 1 a" refers to glycosylated interferon beta.

The activity of interferon beta may e.g. be measured using a reference standard calibrated against the World Health Organization natural interferon beta standard (Second International Standard for interferon, Human Fibroblast GB 23 902 531). The unit is expressed in international units (IU) of antiviral activity per mg of interferon beta-1a determined in an in vitro cytopathic effect bioassay using WISH cells and Vesicular Stomatitis virus.

Conversion Table for MIU and mcg of IFN-Beta

| MIU | 3 | 12 | 18 | 24 |
|---|---|---|---|---|
| mcg | 11 | 44 | 66 | 88 |

"Variants" or "muteins", as used in the fame of the present invention, refer to analogs of IFN-beta, in which one or more of the amino acid residues of natural IFN-beta are replaced by different amino acid residues, or are deleted, or one or more amino acid residues are added to the natural sequence IFN-beta, without diminishing considerably the activity of the resulting products as compared with the wild type IFN-beta. These muteins are prepared by known synthesis and/or by site-directed mutagenesis techniques, or any other known technique suitable therefor.

The terms "variant" or "mutein" in accordance with the present invention include proteins encoded by a nucleic acid, such as DNA or RNA, which hybridizes to DNA or RNA encoding IFN-beta as disclosed e.g. in U.S. Pat. No. 4,738, 931 under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992). Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990).

Any such variant or mutein preferably has a sequence of amino acids sufficiently duplicative of that of IFN-beta, such as to have substantially similar activity to IFN-beta. A functional assay for evaluating whether any variant or mutein has a similar activity as IFN-beta is e.g. the assay measuring the activity of interferon on the cytopathic effect of vesicular stomatitis virus in WISH cells, e.g. described by Youcefi et al., 1985. Thus, it can be determined whether any given mutein has substantially the same activity as IFN-beta by means of routine experimentation.

Any such variant or mutein may have at least 40% identity or homology with the sequence of IFN-beta as disclosed e.g. in U.S. Pat. No. 4,738,931. More preferably, it has at least 50%, at least 60%, at least 70%, at least 80% or, most preferably, at least 90% identity or homology thereto.

Muteins of IFN-beta, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IFN-beta polypeptides may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Examples for of amino acid substitutions in proteins which can be used for obtaining muteins of IFN-beta for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

A special kind of interferon variant has been described recently. The so-called "consensus interferons" are non-naturally occurring variants of IFN (U.S. Pat. No. 6,013,253). Consensus interferons may also be produced according to the invention.

"Functional derivatives" of IFN-beta as used herein covers derivatives which may be prepared from the functional groups which occur as side chains on the residues or the N- or C-terminal groups, by means known in the art, and are included in the invention as long as they remain pharmaceutically acceptable, i.e., they do not destroy the biological activity of the proteins as described above, i.e., the ability to bind the corresponding receptor and initiate receptor signaling, and do not confer toxic properties on compositions containing it. Derivatives may have chemical moieties, such as carbohydrate or phosphate residues, provided such a derivative retains the biological activity of the protein and remains pharmaceutically acceptable.

Derivatives of interferon beta may, for example, include polyethylene glycol side-chains, which may improve other properties of the protein, such as the stability, half-life, bioavailability, tolerance by the human body, or immunogenicity. To achieve this goal, IFN-beta may be linked e.g. to Polyethlyenglycol (PEG). PEGylation may be carried out by known methods, described in WO 92/13095, for example. In particular, PEG-IFN can be prepared in accordance with the teaching of WO 99/55377.

A functional derivative of IFN-beta may comprise at least one moiety attached to one or more functional groups, which occur as one or more side chains on the amino acid residues. An embodiment in which the moiety is a polyethylene glycol (PEG) moiety is highly preferred. In accordance with the present invention, several PEG moieties may also he attached to the IFN-beta.

Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

A "fragment" according to the present invention refers to any subset of IFN-beta, that is, a shorter peptide, which retains the desired biological activity as measurable e.g. in the bioassay described above. Fragments may readily be prepared by removing amino acids from either end of the molecule and testing the resultant for its properties as a receptor agonist. Proteases for removing one amino acid at a time from either the N-terminal or the C-terminal of a polypeptide are known, and so determining fragments, which retain the desired biological activity, may be determined e.g. in the test described by Youcefi et al., 1985, and involves only routine experimentation.

The process for production of interferon beta of the invention may be carried out at a constant temperature, or at varying temperatures. It may e.g. be carried out at 37° C. over the whole process. It may also be carried out at a temperature that is initially, e.g. during the growth phase, at 37° C. and then diminished to 35° C., 33° C. or 30° C. for the production phase.

In a preferred embodiment, the process of the invention comprises a growth phase I, a growth phase II and a production phase, wherein the growth phase I is carried out at about 37° C., the growth phase II is carried out at about 35° C., and the production phase is carried out at about 33° C.

Determination of the end of the phases is well within the knowledge of the person skilled in the art and is determined e.g. on the basis of cell density, glucose consumption or any other metabolic indication. Generally, growth phase I may e.g. be 10 to 12 days. Growth phase II is generally shorter and mainly serves for adapting the cells to a lower temperature. The growth phase II may e.g. be 1 to 2 days.

The process of the invention may be carried out as a fed-batch or a perfusion process. In accordance with the present invention, perfusion is preferred.

Preferably, the process is a perfusion process with a dilution rate ranging from about 1 to about 10, preferably from about 1.5 to about 7 per day.

The term "dilution rate", as defined herein, refers to the dilution rate D, calculated as liter of medium per liter of total system working volume per day (total volume=packed-bed+conditioning tank volume). In accordance with the present invention, the dilution rate may be in a range of e.g. 0.5, 1, 1.5, 1.6, 1.7, 1.8, 1.9, 2, 2.5, 3, 3.5, 4, 4.5, 5, 5.5, 6, 6.5, 7, 7.1, 7.2, 7.3, 7.4, 7.5, 8, 8.5, 9, 9.5, 10, 10.5.

More preferably, the dilution rate is increased within the first two to three weeks of cell culture from an initial value of about 1 to 2 per day to a value of about 7 to 10 per day, particularly during the production phase.

The culturing step of the process of the invention may be carried out in any suitable environment, such as Petri dishes, T-flasks or roller bottles, but preferably in vessels having greater volumes such as e.g. a bioreactor.

When the selection is a perfusion process, the system may e.g. be a stationary packed-bed bioreactor in which cells are immobilized onto solid carriers. This system is easy to operate and with appropriate carriers and culture conditions very high cell density (of ~$10^7$-$10^8$ cell·ml$^{-1}$) can be achieved.

A solid carrier that may be used in accordance with the present invention may e.g. be a microcarrier. Microcarriers are small solid particles on which cells may be grown in suspension culture. Cells are capable of adhering and propagating on the surface of microcarriers. Typically, microcarriers consist of beads, the diameter of which is comprised between 90 µm and 300 µm. Microcarriers can be made of various materials that have proven successful for cell attachment and propagation such as, e.g., glass, polystyrene, polyethylene, dextran, gelatin and cellulose. In addition, the surface of microcarriers may be coated with a material promoting cell attachment and growth such as, e.g., e.g., N,N-diethylaminoethyl, glass, collagen or recombinant proteins. Both macroporous and non-porous microcarriers do exist. Macroporous surfaces give the cells easy access to the interior of the microcarrier after inoculation, and once inside of the microcarrier, the cells are protected from the shear forces generated by mechanical agitation and aeration in the bioreactor.

A further solid carrier that may be used in accordance with the present invention may e.g. be a disk, such as a disk composed of polyester non-woven fiber bonded to a sheet of polypropylene mesh (see, e.g., U.S. Pat. No. 5,266,476). Such disks are usually treated electrostatically to facilitate suspension cells adhering to the disks and becoming trapped in the fiber system, where they remain throughout the cultivation process. Cell density and productivity achieved with cells grown on disks can be up to ten times higher than with cells growing on microcarriers.

The process for the production of glycosylated interferon beta preferably further comprises a step of collecting the interferon beta containing cell culture harvest.

In a preferred embodiment, the cell culture harvest is further subjected to a purification process.

The purification process may be any process leading to interferon beta of the required purity and may contain any combination of purification steps based on chromatography or any other purification technology such as fractionation with salt or the like. The purification is preferably carried out according to the second aspect of the present invention.

In a second aspect, the invention relates to a process for the purification of recombinant interferon from a fluid, comprising the steps of:
  a) Subjecting the fluid to affinity chromatography;
  b) Subjecting the eluate of the affinity chromatography to cation exchange chromatography;
  c) Subjecting the eluate of the cation exchange chromatography to hydrophobic chromatography by RP-HPLC.

Step (a) is preferably carried out on Blue Sepharose, e.g. on a Blue Sepharose fast flow column. Step (b) is preferably carried out on a carboxymethyl resin, e.g. on a CM Sepharose fast flow.

In a preferred embodiment, the purification process of the invention further comprises, before step (a), a step of clarifying the fluid by microfiltration.

In yet a further preferred embodiment, the purification process according further comprising the steps of:
  d) performing ultrafiltration and dialysis,
  e) subjecting the dialysate to size exclusion chromatography,
  f) subjecting the eluate of the size exclusion chromatography to filtration.

Step (f) may be carried out e.g. by micro- or nanofiltration.

Ultrafiltration is useful for removal of small molecular weight components in the eluates resulting from previous chromatrographic steps. Ultrafiltration e.g. allows to remove organic solvent, TFA and salts from the previous step, to equilibrate the interferon beta in the required buffer, or to concentrate the molecule to the desired concentration. Such ultrafiltration may e.g. be performed on ultrafiltration media excluding components having molecular weights below 5 kDa.

If the protein purified according to the process of the invention is intended for administration to humans, it is advantageous to further include steps of virus removal. A virus removal filtration step may e.g. be carried out between steps (d) and (e), or after step (e). More preferably, the process comprises two virus removal steps.

The purity that may be obtained with the purification process according to the invention is preferably >80%, more preferably >90% and most preferably >98%.

The process of purifying interferon beta in accordance with the present invention preferably further comprises a step of formulating the purified interferon beta into a pharmaceutical composition, optionally together with a pharmaceutically acceptable carrier.

The interferon beta to be produced or purified in accordance with the present invention may be expressed by any cell line or clone. However, it is preferred to use a chinese hamster ovary (CHO) cell line, designated DUKX-B11, which lacks DHFR (dihydrofolate reductase) activity, as the host cell for the preparation of glycosylated interferon beta. The DNA sequence coding human interferon-β is e.g. described in U.S. Pat. No. 5,326,859.

A preferred embodiment of the present invention relates to a method for producing recombinant human interferon-β in transfected cells capable of producing at least about 100000 IU of recombinant human interferon-β in specific cellular productivity (IU/10$^6$ cells/24 hours). Preferably, the cells are capable of producing at least about 200000 IU or at least about 200000 IU or at least about 300000 IU or at least about 400000 IU or at least about 500000 IU or at least about 600000 IU of recombinant human interferon beta specific cellular productivity.

Preferably the interferon beta producing cell is a CHO cell which is transfected with a nucleic acid construct comprising at least one promoter/enhancer element functionally linked to the human IFN-β gene. More preferably, the at least one promoter/enhancer element comprises a SV40 promoter/enhancer. Most preferably, the nucleic acid construct comprises at least a first transcription unit composed of the SV40 promoter/enhancer functionally linked to the human IFN-β gene, the human IFN-β gene being functionally linked to the SV40 T Ag early polyadenylation region. It is also highly preferred that the nucleic acid construct further comprises at least a second transcription unit composed of a SV40 promoter/enhancer, a mouse DHFR gene and a SV40 T Ag polyA-containing early polyadenylation region.

Another embodiment of the present invention relates to a nucleic acid construct comprising at least one promoter/enhancer element functionally linked to the human IFN-β gene for being transfected into cells, being characterized in that the transfected cells are capable of producing at least about 100000 IU, at least about 200000 IU or at least about 300000 IU or at least about 400000 IU or at least about 500000 IU or at least about 600000 IU of recombinant human interferon-β in specific cellular productivity (IU/10$^6$ cells/per 24 hours).

Preferably, at least one promoter/enhancer element comprises a SV40 promoter/enhancer. More preferably, the nucleic acid construct comprises at least a first transcription unit composed of the SV40 promoter/enhancer functionally linked to the human IFN-β gene, the human IFN-β gene being functionally linked to the SV40 T Ag early polyadenylation region. Most preferably, the nucleic acid construct further comprises at least a second transcription unit composed of a SV40 promoter/enhancer, a mouse DHFR gene and a SV40 T Ag polyA-containing early polyadenylation region.

The invention further relates to an interferon beta obtainable by a process according to the present invention.

In a further aspect, the invention relates to an interferon beta composition having a unique glycosylation profile. Such interferon beta is preferably produced by a process according to the present invention.

In one embodiment, the glycosylated recombinant human interferon-β protein contains an oligosaccharide structure having two or three fucose saccharides. In a preferred embodiment, the oligosaccharide structure further comprises a disialyl biantennary trifucosylated glycan (NeuAc$_2$.Hex$_5$.HexNAc$_4$.Fuc$_3$).

In a further preferred embodiment, the unique glycosylation pattern further comprises a non sialylated biantennary structure (Hex$_5$.HexNAc$_4$.Fuc); disialylated triantennary structure or disialylated biantennary with N-acetyl lactosamine repeat structures (NeuAc$_2$.Hex$_6$.HexNAc$_5$.Fuc); trisialylated triantennary structure (NeuAc$_3$.Hex$_6$.HexNAc$_5$.Fuc); trisialylated triantennary structure with N-acetyl lactosamine repeat structures or trisialylated tetrantennary (NeuAc$_3$.Hex$_7$.HexNAc$_6$.Fuc); mono sialylated and disialylated biantennary structure with two fucose units (NeuAc.Hex$_5$.HexNAc$_4$.Fuc$_2$, NeuAc$_2$.Hex$_5$.HexNAc$_4$.Fuc$_2$).

Preferably, the unique glycosylation pattern comprises glycans featuring a similar level of N-Acetylneuraminic acid: N-Glycolylneuraminic acid as for natural human protein glycosylation patterns.

In a further preferred embodiment, the interferon beta composition of the invention is characterized by a sialylation profile comprising about 1 to about 5% of unsialylated N-glycans, about 5 to about 25% of mono-sialylated glycans, about 55 to about 75% of disialylated N-glycans, about 10 to about 25% of tri-sialylated N-glycans.

A further aspect of the present invention relates to the use of interferon beta in accordance with the present invention for the manufacture of a medicament for treatment of human disease, in particular multiple sclerosis, cancer, or viral infections.

The multiple sclerosis may be selected from the group consisting of relapsing, non-relapsing and early onset multiple sclerosis.

In a further aspect, the invention relates to a method of treating a subject in need of treatment with interferon-β according to the invention, comprising administering to the subject recombinant human interferon-β protein as described herein.

Preferably, the treatment is for multiple sclerosis. More specifically, the multiple sclerosis may be selected from the group consisting of relapsing, non-relapsing and early onset multiple sclerosis.

Alternatively, the treatment is an anti-tumor treatment.

In a further alternative, the treatment is an anti-viral treatment.

In a further aspect of the present invention, the invention relates to a pharmaceutical composition comprising, as an active ingredient, an isolated, purified, recombinant human interferon-β composition as described herein and a pharmaceutically acceptable carrier for administration of the pharmaceutical composition. Preferably, the pharmaceutical composition having anti-tumor or anti-viral activity, or activity against multiple sclerosis, comprises, as an active ingredient, an isolated, purified, recombinant human interferon-β protein as described herein and a pharmaceutically acceptable carrier for administration of the pharmaceutical composition.

In yet a further aspect of the present invention, the invention relates to an article of manufacture comprising packaging material and a therapeutically effective amount of an isolated, purified recombinant interferon-β protein, wherein the packaging material comprises a label or package insert indicating that the recombinant human interferon-β protein as described herein can be administered to a human for treatment thereof.

The isolated, purified, recombinant human interferon-β protein or pharmaceutical composition as described herein is preferably used for the manufacture of a medicament for treatment of relapsing, non-relapsing and early onset multiple sclerosis. Dosing regimens for a particular subject (patient) can easily be determined by one of ordinary skill in the art, as these regimens are well known in the art.

Reference is now made to the following examples, which together with the above description, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed.

(1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Preparation of a Chinese Hamster Ovary (CHO) Clone Producing IFN-Beta at High Levels This Example describes the generation of an interferon beta producing CHO clone.

The basic procedure, particularly with regard to the preparation of the expression plasmid, is described in Mory et al. (1981).

Figure 1:
FIG. 1 shows a flowchart of the method used for generating an interferon beta producing cell line.
Figure 1:
Figure 1:
Figure 1:
Figure 1:
Figure 1:
Figure 1:

An overview over the process of generating the clone is depicted in FIG. 1. A DNA fragment comprising the human interferon-β coding region was isolated from a human peripheral blood cell genomic DNA library. A DHFR-deficient CHO cell line was transfected with a recombinant plasmid containing both the human IFN-β coding sequence and the mouse DHFR gene as a selectable and amplifiable marker. After selection in thymidine-free medium, gene amplification with methotrexate (MTX), and cloning, a cell producing IFN-β-1a at high levels was isolated. The cells were subjected to genotypic and phenotypic characterization.

Construction of the Expression Plasmid Carrying the hIFN-β and the mDHFR Genes

An expression vector containing both, the genomic human IFN-β coding sequence and the mouse DHFR resistance gene was constructed. This construction eliminated the necessity of co-transfection of the CHO host cells with two separate plasmids, one comprising the IFN-β coding sequence and the second comprising the mouse DHFR sequence, as known e.g. from Chernajovsky et al., 1984.

The expression vector containing the IFN-β coding sequence was devoid of the IFN-β 3'UTR and thus of the IFN-β polyadenylation region.

The expression vector of the invention therefore contained two transcription units, a first IFN-β transcription unit composed of the SV40 promoter/enhancer, the human IFN-β coding sequence and the SV40 T Ag early polyadenylation region, and a second DHFR transcription unit composed of the SV40 promoter/enhancer, the mouse DHFR gene and the SV40 T Ag polyA-containing early polyadenylation region.

These transcription units were followed by sequences from the pBR322 plasmid carrying the ColEI bacterial origin of replication and ampicillin resistance gene.

The structure of the expression vector was verified by restriction map analysis and by complete sequencing (double-stranded, automated sequencing). The correct sequence of the fragments used for its construction was confirmed in both directions.

Description of the Host Cell

A Chinese hamster ovary (CHO) cell line, designated DUKX-B11, which lacks DHFR (dihydrofolate reductase) activity, was used as the host cell. The cell line was isolated from the CHO-K1 cell line, requiring proline (Kao and Puck, 1968) by mutagenesis with ethyl methanesulfate followed by gamma irradiation. DHFR deficient mutants were selected by exposure to high specific activity [$^3$H]-deoxyuridine (Urlaub and Chasin, 1980).

Full deficient mutants require glycine, hypoxanthine and thymidine for growth. The central role of DHFR in the synthesis of nucleic acid precursors, together with the sensitivity of DHFR-deficient cells to analogs such as methotrexate (MTX), present two major advantages. Firstly, transfection of such DHFR-deficient cells with plasmids containing a DHFR gene allows the selection of recombinant cells that grow in thymidine-free medium. Secondly, culture of these cells in selective media containing increasing concentrations of MTX results in amplification of the DHFR gene and the associated DNA (Kaufman and Sharp 1982, and Sambrook, J., Fritsch, E. F., Molecular Cloning: A laboratory manual. Cold Spring Harbor Laboratory Press, Cold Spring Harbor, N.Y., 1989).

Generation of the Clone

As outlined in FIG. 1, anchorage-dependent, DHFR-deficient CHO cells were transfected by the calcium phosphate precipitation procedure (Graham F L and Van Der E B, 1973; Busslinger, et al., 1981) with the plasmid containing both the h-IFN-β coding sequence and the mDHFR marker gene described above. To amplify the transfected gene, selected clones were submitted to MTX (methotrexate) treatment. The clones were isolated after MTX selection.

Transfection

The CHO DHFR-deficient cell line DUKX-B11 was cultured in Ham's Nutrient Mixture F12 supplemented with 10% FBS, at 37° C., 5% $CO_2$.

The day before transfection, the CHO DUKX-B11 cells were seeded at $5\times10^5$ cells/9 cm plate. $CaPO_4$-DNA co-precipitates were prepared by mixing the vector DNA, dissolved in 0.45 ml of 10 mM Tris-HCl pH 7.9, 0.1 mM EDTA, with 0.05 ml of a 2.5M $CaCl_2$ solution.

Next, 0.5 ml of 280 mM $Na_2HPO_4$, 50 mM HEPES pH 7.1 was added with gentle shaking and the mixture was kept for 30-40 minutes at room temperature, to allow precipitation. After adding the $CaPO_4$-DNA to the cells for 30 minutes, 9 ml of cell culture medium were added and the cells returned to the incubator for 4 hours. Thereafter, the medium was removed and the cells osmotically shocked with 10% glycerol in medium, for 4 minutes. The cells were then trypsinized and subcultured at 1:4 to 1:10 split ratio in selective medium consisting of Dulbecco's Modified Eagles Medium (DMEM) lacking thymidine but supplemented with 150 µg/ml proline and 10% dialyzed FBS. The cultures were kept at 37° C. and 8% $CO_2$ and the selective medium was changed every 3-4 days.

Isolation of a Constitutive hIFN-β Producing Cell Line

Interferon beta producing cells were isolated after 10-12 days by trypsinization with 3 mm trypsin-soaked paper-discs. Forty-three clones were picked, individual clones were grown and the cell culture supernatants tested for hIFN-β production by ELISA. Three clones producing more than 30,000 IFN-β IU/$10^6$ cells/24 hours were selected for gene amplification.

Each of the clones was subjected to culture with low concentrations of MTX. The entire cell population that survived the treatment was subjected to higher MTX concentrations. Subcloning and clone selection were performed only after the last amplification stage. The selected high producers (more than 400,000 IU/$10^6$ cells/24 hours) were subjected to clone stability studies. A relatively stable high producer clone was selected and subcloned. From the resulting clones, a high producer stable clone was selected.

Amplification increased production levels (specific productivity) of IFN-β-1a from 30,000 to 500,000 IU/$10^6$ cells/24 hours, as determined by ELISA.

Northern blot analyses were performed after the initial isolation of the clones of high IFN-β-1a productivity. A single hIFN-β mRNA of about 0.9 kb, as expected from the expression construct, was expressed (data not shown).

For the Northern blot analysis of total RNA from primary clones, the blot was prepared as follows.

Twenty µg of total RNA were separated by electrophoresis on agarose formaldehyde gels. RNA was transferred to a nylon membrane and hybridized to an IFN-β DNA probe. Size markers (M) are 28S and 18S rRNA, which correspond to 4700 and 1900 nucleotides, respectively (not shown).

Productivity

Cellular productivity was then tested as follows. The tissue culture (growth) medium was DMEM (Dulbecco's Modified Eagle's medium), supplemented with proline (150 mg/l) and 10% FBS (fetal bovine serum) or in serum-free medium, e.g. Ex-Cell 302 from JRH.

Cells from the interferon producing clone were seeded in TC80 flasks ($2\times10^6$ cells/flask) in 30 ml growth medium (either DMEM and FBS, or serum-free medium). When initial confluency was reached, as determined by microscopic examination, the growth medium was replaced with 20 ml of fresh medium and the cultures incubated at about 32° C. for 24 hours. Samples of the culture medium were obtained from each flask. IFN-β-1a level was determined by ELISA from the culture medium with a commercial ELISA kit (for example, the Toray ELISA kit from Toray, Japan).

Specific cellular productivity was calculated by multiplying the IU/ml of IFN-β-1a produced per 24 hours by the volume per TC80 flask and dividing by the total cell number (in millions) per flask.

Results and Conclusions

The interferon beta producing cell clone was a stable cell line, having a high production capacity for recombinant human interferon-β in the range of about 100,000 IU in specific cellular productivity (IU/$10^6$ cells/24 hours) and about 600,000 IU in specific cellular productivity. The mean productivity of the new cell line was 556,000±119,000 IU/$10^6$ cells/24 hrs.

General cellular morphology was also examined by phase contrast microscopy one to four days after seeding. Morphology was documented with photomicrographs (not shown). The results show that at low density (24 to 48 hrs after seeding) the cells exhibited rounded, spindle-shaped morphology (results not shown). At confluency, the cells form dense monolayers comprised of elongated, spindle shaped and smaller, tightly packed, epithelial-like cells (results not shown). The morphological characteristics exhibited by these cells were typical of CHO cells.

DNA Sequence Determination of the hIFN-β Coding Region in Cells of the Clone

PCR DNA products derived from the hIFN-β messenger RNA (mRNA) were used to determine the coding region nucleotide sequences as the mRNA sequence provides direct proof that the RNA transcripts are processed correctly.

Procedure for DNA Sequencing cDNA and PCR Reactions

Total cellular RNA was prepared from the cells in the exponential stage of growth in T-flask cultures (Chomczynski and Sacchi, 1987). Complementary DNA (cDNA) was synthesized from the mRNA samples in a reaction which contained 2 micrograms (µg) of total RNA, 0.5 µM random hexamers, 2.5 mM $MgCl_2$, 1× PCR II buffer [10 mM Tris-HCl (pH 8.3), 50 mM KCl], 0.5 mM each of dATP, dCTP, dGTP, and dTTP, 40 units of RNase Inhibitor, and 200 units of Reverse Transcriptase in a final volume of 100 µl.

The RNA template, primer and nuclease-free water were combined and incubated at 65° C. for 10 minutes and were then placed in an ice bath. The remaining components were added and the reaction was incubated at 42° C. for 60 minutes, then 70° C. for 15 minutes and was then held at 4° C. indefinitely. The RT products (cDNAs) were stored at −20° C. until further use. As a control, a reaction with all components except the reverse transcriptase was prepared. The "no RT" control is to exclude the unlikely possibility that the RNA preparations had DNA contamination.

PCR amplification was done using primers SRB1 AP1 and AP2 for the cDNA templates. Sequences for these primers are as follows:

```
SRB1 AP1: CCTCGGCCTCTGAGCTATTC (SEQ ID NO: 1)

SRB1 AP2: CACAAATAAAGCATTTTTT  (SEQ ID NO: 2)
```

The PCR reactions consisted of the following: 4.0 µl of cDNA reaction mixture, 50 pmol of each of the primer pair, and 25 µl HotStarTaq™ Master Mix in a reaction volume of 50 µl. The reactions were heated at 95° C. for 15 minutes followed by 30-35 cycles of: (a) 94° C. for 30 seconds, (b) 55° C. for 30 seconds, and (c) 72° C. for 1 minute. A final cycle, identical to the first 30-35, but with the 72° C. incubation time extended to 10 minutes, was then done.

The hIFN-β PCR products were purified by low melting point (LMP) agarose gel electrophoresis followed by extraction using the QIAquick gel extraction kit (Qiagen).

Sequencing of Amplified DNA

The PCR products were sequenced directly with the Big Dye™ Terminator Cycle Sequencing Ready Reaction Kit with AmpliTaq® DNA Polymerase. All sequencing reactions were analyzed on 5.75% Long Ranger™ gels on ABI373-S automated DNA sequencers. The raw data were tracked and analyzed using ABD Analysis software.

Results

PCR amplification resulted in the generation of the predicted approximate 815 bp fragment. No PCR products were observed for the "no RT" control nor for the other negative controls.

Complete sequence data were obtained for the protein-coding region of the hIFN-β gene; all nucleotides were read on two or more electropherograms (data not shown). When the sequences were compared to the expression vector, no differences were found (data not shown).

Conclusions

The sequencing data demonstrate that the hIFN-β gene integrated into cells of genome of the clone is correctly transcribed into hIFN-β mRNA.

Determination of Gene Copy Number

The gene copy number was determined by Southern blot analysis of BamHI digests.

The specific primers used to build the probes for the gene copy number analysis are the following:

```
(i)
5': PR221626: ATGACCAACAAGTGTCTCCTCC (SEQ ID NO: 3)

(ii)
3': PR231217 ACTTACAGGTTACCTCCGAAAC (SEQ ID NO: 4)
```

Procedures for Genomic DNA Preparation and Southern Blotting

Genomic DNA was isolated from exponentially growing T-flask cultures of the cells using a modification of the salting out method (Martinez et al., 1998). Briefly, the cells were resuspended in a Tris-NaCl-EDTA buffer and then lysed with a Tris-NaCl-EDTA-SDS buffer. This suspension was treated overnight with proteinase K. After addition of a saturated salt solution and centrifugation, the genomic DNA was precipitated by addition of isopropanol to the aqueous phase. Following a 70% ethanol wash, the DNA pellet was resuspended in a TE/RNase A solution (10 mM Tris-HCl pH 8.0, 1 mM EDTA, 20 µg/ml RNaseA).

Aliquots of all the genomic DNA preparations were digested with AflIII, BbsI, BglI, DraI, HincII, PstI, and XmnI. Standards were prepared by digestion of the expression vector DNA sample with the same restriction endonucleases used for the genomic samples. The DNA was size-fractionated by electrophoresis in agarose gels and then transferred in 10×SSC to nylon membranes by capillary action. The amount of genomic DNA loaded was 0.5 µg. Blots were prepared for hybridization to a $^{32}$P-labeled hIFN-β fragment that was PCR amplified from the plasmid using the primers indicated above. Prehybridization and hybridization was done at 65° C.

Size determinations were made based on the migration of the bands as visualized by $^{32}$P on an autoradiograph. The expression vector was used as the control.

Copy number determinations were based on relative $^{32}$P levels in the bands as quantitated on a model 445SI Phospho-Imager™ (Molecular Dynamics; Sunnyvale, Calif.). Autoradiographs were photographed to provide a record of the results (data not shown).

Results

Size determinations of fragments generated for the interferon beta producing cells of the clone were compiled for all digests.

Enzyme digestion of the DNA extracted from the interferon beta producing cell line resulted in the production of prominent bands that matched those predicted from the expression vector for the BamHI, BglI, DraI and HincII digests. A very faint band (~1.77 kb) was observed with the BglI-digested genomic DNAs, most likely a result of incomplete digestion. These restriction enzymes flank the hIFN-β expression unit indicating that an intact, functional, full-length unit has integrated into the genome.

In the remaining digests, differences in the banding patterns were observed between the expression vector and the genomic DNAs. This is not unexpected as some rearrangement must occur when the circular vector integrates into the CHO cell genome.

The copy number levels determined for the cells of the clone were on average 96-105 copies per cell. For example, for one group of cells, the average gene copy number (n=3) was 105, with an standard deviation of 23 and a CV (%) of 22.

Determination of mRNA Size

Total RNA was isolated from exponentially growing interferon beta producing cells and untransfected CHO DUKX cells (Chomczynski and Sacchi, 1987). The probes used included a $^{32}$P-labeled hIFN-β probe prepared as described in section "Determination of gene copy number" and a control G3PDH cDNA probe (Clontech; Palo Alto, Calif.).

Procedure

Total RNA, 5 µg per lane, was size-fractionated by electrophoresis in agarose gels that contained formaldehyde as a denaturant. Samples were loaded in duplicate sets. The RNA was transferred in 10×SSC to nylon membranes by capillary action. Prehybridization and hybridization were done at 65° C. in the modified Church and Gilbert solution described in section "Restriction endonuclease map analysis". The blots were hybridized to a $^{32}$P-labeled hIFN-β probe and a control G3PDH cDNA probe. The band sizes were estimated from an autoradiograph of the blots.

Results and Conclusions

One major IFN-β mRNA species was observed for the cells. The mRNA size was estimated to be 0.9 kb mRNA. This size correlates well to an mRNA starting at the SV40 transcription initiation site and resulting in a transcript of about 800 nucleotides without considering the polyA tail.

General Conclusions and Summary

The phenotypic and genotypic studies on the interferon beta producing cells confirmed the identity and consistency of the cells.

The chromosomal integration of the hIFN-β gene into the CHO cells genome was demonstrated by in-situ hybridization studies.

Comparison of restriction endonuclease mapping patterns, DNA sequences and mRNA analyses of cells showed no evidence of gross DNA rearrangements or point mutations of the hIFN-β gene.

The hIFN-β gene copy number levels were measured by Southern blot analysis of DNA extracted from the cells of the clone according to the present invention. The results showed that gene copy number levels were in the same ranges for all cells, independently of the population doubling levels.

Northern blot analysis of RNA prepared from the cells showed a single band of approximately 0.9 kb in size.

Sequence analyses of the cDNA from the cells confirmed the correctness of the mRNA sequence, while the genomic DNA sequences of the 5' and 3' control regions of the hIFN-β gene verified the integration of the complete IFN-β transcription unit.

In conclusion, it was demonstrated that the interferon beta producing cells synthesized hIFN-β mRNA transcripts with the correct protein coding region sequence, indicating that the interferon beta producing cells produce human recombinant IFN-β (IFN-β-1a) with the correct primary amino acid sequence.

For the genotypic characterization, restriction map analyses were performed on the interferon beta producing cells. Multiple digests were separated by agarose gel electrophoresis, transferred to nylon membranes and hybridized to labelled probes specific for the hIFN-β. Consistent restriction fragment profiles, indicated the integration of an intact functional hIFN-β expression unit, in all the cell banks.

The hIFN-β gene copy numbers were determined by Southern blot analysis of DNA extracted from the interferon beta producing cells (data not shown). The results show gene copy numbers to be about 100 copies per cell, which is about four times higher than for the clone described in the literature (Chernajovsky et al., 1984).

By Northern blot analysis, one mRNA of about 0.9 kb, coding for the hIFN-β gene, was identified for the cells from the clone (data not shown).

The hIFN-β cDNAs prepared from the cells' mRNAs were sequenced and the results showed that for the cells, the hIFN-β gene sequence was 100% identical to the expected sequences. Thus, the hIFN-β gene is correctly transcribed into mRNA.

The genomic DNA sequence of the 5' and 3' regions flanking the hIFN-β gene was determined for the cells of the clone and found to be 100% identical to the corresponding sequences of expression vector and the published sequence of the hIFN-β gene.

The single chromosomal integration of the hIFN-β gene was also demonstrated by fluorescent in-situ hybridization (FISH, results not shown).

The analyses presented above also demonstrated the stability of the production line.

It can thus be assumed that the transfected gene is stably integrated in the interferon beta producing cells' genome.

Example 2

Process for the Production of Interferon Beta

The overall goal of this experiment was to develop a process for producing IFN beta-1a from the clone described in example 1 under serum-free conditions.

The serum-free process was developed at 75 L bioreactor scale with internal packed bed Fibra-Cel® carriers.

The cells were thawed and expanded over 21 days in a commercially available serum-free medium having the following modifications:

TABLE 1

| Modification of serum-free medium | |
|---|---|
| Ingredients | Composition in % (w/w) |
| HEPES | 20 mM |
| Proline | 1 mM |
| Phenol Red | 15 mg/L |
| Sodium chloride | 6150 mg/L |

$30 \times 10^9$ cells were seeded in the 75 L bioreactor (high seeding).

The runs were divided into the following phases:
a growth phase I at 37° C. (until working day 2 or working day 4 or when the glucose consumption rate (GCR) was $\geq 2.0 \pm 1.0$ g·L$^{-1}$·d$^{-1}$)
a growth phase II at 35° C. (until working day 7 or when GCR$\geq 8.0 \pm 0.5$ g·L$^{-1}$·d$^{-1}$)
a production phase at 33° C.

This temperature strategy resulted in a productivity around $6.0 \times 10^6$ IU/ml bio per day. This productivity is about five times higher than the productivity of the clone described in the literature (Chernajovsky et al., 1984) in serum-containing medium.

It was further tested whether addition of N-Actey-Cyteine (NAC) alone or in combination with Zinc (NAC+Zn) had a beneficial effect on productivity. Addition of NAC or NAC+Zn increased the productivity to around $12 \times 10^6$ IU/ml bio per day at the end of the run.

A 66% lower seeding cell density ($1.3 \cdot 10^9$ cells) was also tested in order to evaluate its impact on growth phase duration, metabolism and productivity.

The metabolism and productivity were not affected by low seeding. The only impact of low seeding was the addition of two days to the growth phase.

In summary, the final conditions used for the production of interferon beta were as follows:

| | Temperature | |
|---|---|---|
| | Growth:<br>37° C.⇒ 35° C. | Production:<br>33° C. |
| Dilution rate | 1.6⇒ 7.2 Day$^{-1}$ | |
| pH | 7.0 | |
| pO$_2$ | 70% | |

Example 3

Purification of the Interferon Protein Product

The purification process of the IFN-β-1a from cell culture supernatant included four chromatographic and four filtration stages, as shown in FIG. 2. The purification stages were performed in the following order:
Stage I: Harvest clarification by filtration
Stage II: Affinity chromatography on a Blue Sepharose 6 fast flow (6 FF) column;
Stage III: Ultrafiltration
Stage IV: Cation exchange chromatography using preferably a CM Sepharose FF column;
Stage V: Hydrophobic chromatography RP-HPLC;
Stage VI: Ultrafiltration and dialysis;
Stage VII: Size Exclusion (SE) chromatography;
Stage VIII: Microfiltration.

The purification of the active ingredient started with dye affinity chromatography on Blue Sepharose 6 FF (BS 6 FF), which was the major purification stage. The amount of host cell derived proteins as well as DNA from ruptured CHO cells was reduced by several orders of magnitude and therefore IFN-β-1a in the BS 6 FF eluate was significantly enriched. Before the eluate was loaded on to the next column ultrafiltration was performed to reduce the solution volume and exclude low molecular weight material.

To obtain highly purified IFN-β-1a three main types of column-based protein separations have been chosen. Ion-exchange chromatography on CM-sepharose FF resin removes nucleic acid and FBS/CHO derived proteins. Reverse phase HPLC reduced pyrogens, residual host cell derived proteins and degraded forms of IFN-β-1a. A final polishing stage of gel filtration was performed using Sephacryl S-100 HR resin. The eluate was microfiltered (0.22 μm) and stored at −70° C. or below.

All starting materials used for preparation of buffers and cleaning solutions complied with the Ph. Eur. and/or USP or are of analytical or reagent grade.

Example 4

Sialylation Analysis

The purified IFN-beta was subjected to analysis of the sialylation profile by ES-MS (Electro Spray-Mass Spectrometry), with the following results:

|  | Run 1 | Run 2 |
| --- | --- | --- |
| Non sialylated | 2% | 4% |
| Mono-sialylated | 10% | 22% |
| Di-sialylated | 69% | 59% |
| Tri-sialylated | 20% | 16% |

Example 5

Glycoform Analysis

In order to further analyze IFN-β-1a obtained from the new process, the glycoforms of the protein were analyzed. As previously described, glycosylated proteins often occur as a mixture of different glycoforms, or proteins having different saccharide structures in their glycosylation. Various techniques were used to analyze these glycoforms, as described in greater detail below, including electrospray mass spectroscopy, FAB-MS, MALDI-MS, tandem mass spectroscopy (MS/MS) and GC-MS (linkage studies). These different techniques all showed that of the different saccharide structures studied, one such structure was newly present in the IFN-β-1a obtained from the clone.

Glycoform Distribution Determination by Electrospray Mass Spectroscopy
Method
IFN-β-1a bulk samples of interferon beta obtained by the clone using electrospray mass spectrometry (ES-MS). The method is e.g. described by Fenn, et al., (1989).

Figure 3:
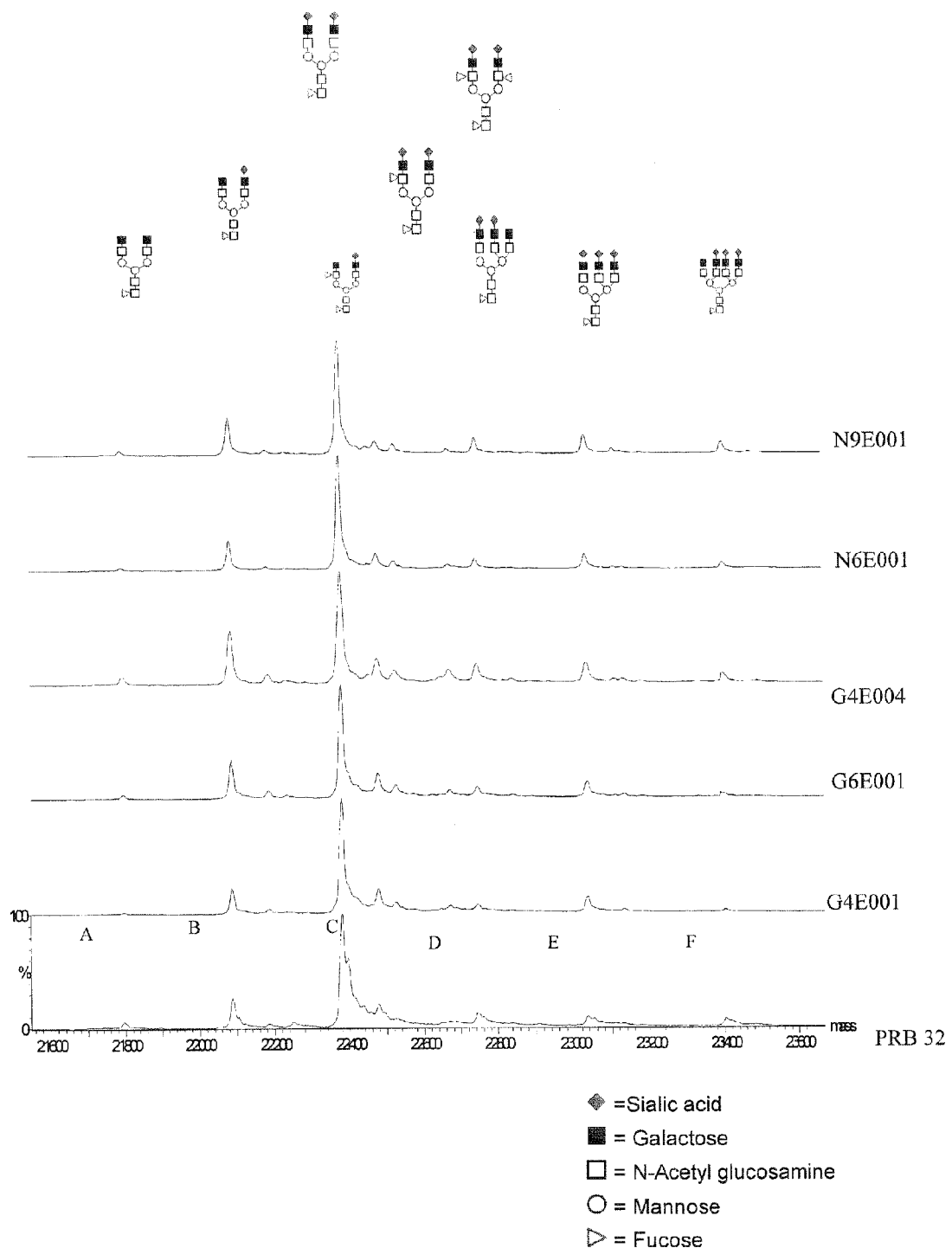
FIG. 3 shows the ES-MS transformed spectra of IFN-β-1a batches wherein a schematic drawing of the oligosaccharides structure is shown on top.
Figure 4:
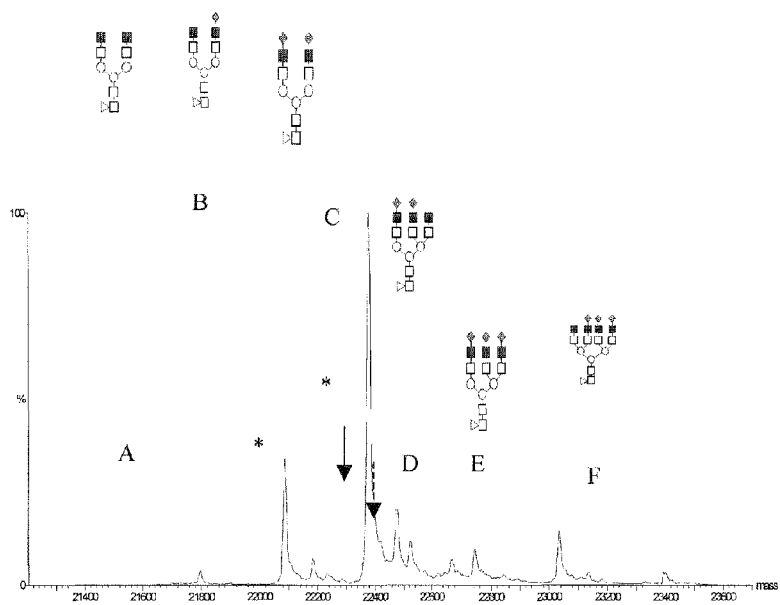

MS/MS of glycans. This technique permitted rapid monitoring of the glycoform distribution of the bulk samples at the molecular mass level. This method is e.g. described by Domon, B. and Costello, C E (1988).
Results
The results are presented in FIGS. 3-5. For all Figures, schematic drawings of the various oligosaccharides are shown on top of each peak. FIGS. 3 and 4 show the ES-MS transformed spectra of several IFN-β-1a batches from interferon beta obtained by the new process.

In all batches tested, the major glycoforms were the core-fucosylated disialyl (peak C) and monosialyl (peak B) biantennary carbohydrate structures and the minor glycoforms corresponded to the core-fucosylated non-sialylated biantennary (peak A), the core-fucosylated triantennary trisialylated (peak E) and 2 other core-fucosylated minor complex structures (peaks D and F).

Minor signals at 22524 Da±0.01%, attributed to disialyl biantennary difucosylated glycans (NeuAc$_2$.Hex$_5$.HexNAc$_4$.Fuc$_2$), were detected by ES-MS in samples of IFN-β-1a derived from interferon beta obtained by the new process. This glycoform can also be defined as biantennary glycan with sialyl Lewis x (Le$^x$) antenna. It should be noted that the Lewis x (Le$^x$) glycan, composed of Hex. HexNAc.Fuc structure, is commonly found in glycoproteins on the surfaces of both lymphocytes (L-selectin) and specialized endothelial cells (Cummings, 1999; Dell and Morris, 2001).

Another minor glycoform centered at a mean molecular weight value of 22670 Da±0.01%, with average amount of 4% of all glycoforms and attributed to a disialyl biantennary trifucosylated glycan (NeuAc$_2$.Hex$_5$.HexNAc$_4$.Fuc$_3$) was detected by ES-MS in the IFN-β-1a batches from interferon beta obtained by the new process, independently of the production scale. The average amount of this minor glycoform is of 4%, with a SD of 0.90.
Conclusions
The glycoform pattern of IFN-β-1a derived from interferon beta obtained by the new process was analyzed by ES-MS.

The minor signals, attributed to difucosylated glycans, found by ES-MS in IFN-β-1a from interferon beta obtained by the new process, were detected by MALDI-MS. One additional minor glycoform (average of 4% of total glycoforms), attributed to a trifucosylated structure, was detected by ES-MS in the product from interferon beta obtained by the new process as well.

Carbohydrate analysis by FAB-MS, MALDI-MS, tandem mass spectroscopy (MS/MS) and GC-MS (linkage studies)

IFN-β-1a bulk samples derived from interferon beta obtained by the new process were subjected to extensive carbohydrate characterization studies. The carbohydrate composition of IFN-β-1a was obtained using FAB-MS, MALDI-MS, Nanospray-MS/MS analyses and linkage studies (GC-MS) of permethylated IFN-β-1a following tryptic and peptide N-glycosidase F digestion. Glycosylation site determination was accomplished by FAB-MS analyses of chymotryptic peptides previously digested with trypsin and N-glycosidase F.
Method
The tryptically cleaved peptide glycopeptide mixture from the IFN-β-1a was treated with the enzyme peptide-N-glycosidase F (e.g. as described by Tarentino et al. 1985).

After stopping the reaction (by freeze-drying), the resulting digest was purified by C18 Sep-pak cartridge. Carbohydrates eluting in the 5% acetic acid fraction were permethylated using NaOH/methyl iodide, as described e.g. by Costello (1997).

A portion of the permethylated glycan was analyzed by positive ion FAB-MS (obtained in low mass ranges for fragment ions and high mass ranges for molecular ions), as described e.g. by Barber, et al. (1981) and Taylor (1983).

MALDI-mass spectrometry was performed as e.g. described by Hillenkamp, et al., 1991.

Nanospray-mass spectrometry was performed as described e.g. by Wilm and Mann 1996.

The remainder of permethylated oligosaccharides were used for linkage analysis by gas liquid chromatography/mass Spectrometry (GC/MS)-following derivatization, as described e.g. by Gray, 1990.

Finally, in order to observe the peptide containing the Asn 80 potential glycosylation site, the tryptic peptides were digested with peptide N-glycosidase F and purified by Sep-pak. The propanol fractions (20%-40%) of the Sep-pak were sub-digested with chymotrypsin and analysed by FAB/MS.

Results

MALDI and FAB-MS of the Permethylated Carbohydrates

The study was conducted on protein from interferon beta obtained by the new process. A representative MALDI spectrum is presented in FIG. 6. The corresponding list of m/z signals observed in the permethylated spectra (MALDI-MS and FAB-MS) is presented in Table 3.

The results of all the batches indicated the presence of a predominant disialylated biantennary structure having the composition of $NeuAc_2.Hex_5.HexNAc_4.Fuc$, and a monosialyl biantennary structure having the composition of $NeuAc.Hex_5.HexNAc_4.Fuc$. Non-fucosylated glycans were not observed.

Minor signals possibly corresponding to the following oligosaccharide structures were also observed in all batches:
Non sialylated biantennary structure ($Hex_5.HexNAc_4.Fuc$)
Disialylated triantennary structure or disialylated biantennary with N-acetyl lactosamine repeat structures ($NeuAc_2.Hex_6.HexNAc_5.Fuc$)
Trisialylated triantennary structure ($NeuAc_3.Hex_6.HexNAc_5.Fuc$)
Trisialylated triantennary structure with N-acetyl lactosamine repeat structures or trisialylated tetrantennary ($NeuAc_3.Hex_7.HexNAc_6.Fuc$)
Mono sialylated and disialylated biantennary structure with two fucose units ($NeuAc.Hex_5.HexNAc_4.Fuc_2$, $NeuAc_2.Hex_5.HexNAc_4.Fuc_2$)
Minor amounts of trifucosylated structures ($NeuAc_2.Hex_5.HexNAc_4.Fuc_3$) were also observed in the batches derived from the interferon beta obtained by the process according to the invention, but were absent in reference IFN-β-1a
Minor amount of N-glycolylneuraminic acid as part of the sialic acids of the glycans.

The relative abundance of N-glycolylneuraminic acid was calculated from the peak heights of signals in the permethylated N-linked glycan FAB and MALDI-TOF data.

As expected the IFN-β-1a glycoforms contain mainly N-Acetylneuraminic acid like most human glycoproteins.

Nanospray MS/MS

In order to further confirm the structures of the trace amounts of N-linked multi-fucosylated oligosaccharide structures, MS/MS analysis was carried out on the permethylated oligosaccharides of signals at m/z 919, 1040 and 1098 which are consistent with the triply charged ions ($[M+3H]^{3+}$) for $NeuAc.Hex_5.HexNAc_4.Fuc_2$, $NeuAc_2.Hex_5.HexNAc_4.Fuc_2$ and $NeuAc_2.Hex_5.HexNAc_4.Fuc_3$ respectively. The A type ions observed in the MS/MS spectrum confirmed the following structure attributions:

TABLE 2

| MS Signal (m/z) | IFN Beta from new process | Attribution by MS/MS |
| --- | --- | --- |
| 919 | Not observed* | NeuAc•Hex$_5$•HexNAc$_4$•Fuc$_2$ |
| 1040 | + | NeuAc$_2$•Hex$_5$•HexNAc$_4$•Fuc$_2$ |
| 1098 | + | NeuAc$_2$•Hex$_5$•HexNAc$_4$•Fuc$_3$ |

*A corresponding signal was however observed by MALDI

Linkage Analysis by GC/MS

Complex GC chromatograms were obtained for all tested batches from interferon beta obtained by the new process with some impurity peaks originating from the derivatizing reagents. GC retention time comparison with a standard mixture of partially methylated alditol acetates run under the same GC conditions allowed provisional assignments of the sugar containing peaks.

Linkage analysis results of all samples were essentially the same, showing the presence of 4-linked N-acetylglucosamine (4-GlcNAc), 4,6-linked N-Acetylglucosamine (4,6-GlcNAc), 3,6-linked Mannose (3,6-Man), 2-linked Mannose (2-Man), terminal Galactose (t-Gal), 3-linked Galactose (3-Gal) and terminal Fucose (t-Fuc), strongly supporting the FAB-MS data. 2,6-linked Mannose was also observed as a minor component in all samples, indicating the presence of some triantennary structures. The postulated major oligosaccharides structures observed in IFN-β-1a bulk samples are presented in FIG. 5.

These data suggest that the main carbohydrate moiety is a core fucosylated biantennary structure with one and two sialic acid residues.

N-Glycosylation Site by FAB-MS of the Chymotryptic Digests

For all IFN-β-1a batches tested a minor FAB-MS signal was observed which was assigned to the sodiated peptide residues 80-88 (D.E.T.I.V.E.N.L.L+Na$^+$) with Asn-80 converted to Aspartic acid following release of the carbohydrate with peptide N-glycosidase F. This experiment provides supporting evidence that Asn-80 is indeed glycosylated.

FIG. 6 shows the MALDI spectrum of IFN-β-1a with permethylated glycans (list of signals in Table 3). Again, as shown in the Table and the accompanying Figure, the IFN-β-1a obtained from the process according to the present invention contains the trifucose structure, $NeuAc_2.Hex_5.HexNAc_4.Fuc_3$ as previously described.

TABLE 3

The list of signals in the permethylated spectra of IFN-β-1a obtained by new process following tryptic and peptide N-glycosidase F digestion

| Signals m/z (G6E001) | Possible Assignment |
| --- | --- |
| Low Mass | |
| 344.2 | NeuAc$^+$ (−methanol) |
| 376.2 | NeuAc$^+$ |
| 406.3 | NeuGc$^+$ |
| 432.3 | Hex•HexNAc$^+$ (−methanol) |
| 464.3 | Hex•HexNAc$^+$ |

TABLE 3-continued

The list of signals in the permethylated spectra of IFN-β-1a obtained by new process following tryptic and peptide N-glycosidase F digestion

| Signals m/z (G6E001) | Possible Assignment |
|---|---|
| 793.5 | NeuAc•Hex•HexNAc⁺ (−methanol) |
| 825.5 | NeuAc•Hex•HexNAc⁺ |
| 855.5 | NeuGc•Hex•HexNAc⁺ |
| 999.5 | NeuAc•Hex•HexNAc(Fuc)⁺ |
| High mass | |
| 2142.6 | — |
| 2227.8 | Fragment ion |
| 2244.8 | Hex$_5$•HexNAc$_4$•Fuc [M + Na]⁺ |
| 2387.8 | Hex$_4$•HexNAc$_4$•Fuc$_3$ [M + Na]⁺ |
| 2417.8 | Hex$_5$•HexNAc$_4$•Fuc$_2$ [M + Na]⁺ |
| N/D | NeuAc•Hex$_5$•HexNAc$_4$•Fuc [M + Na]⁺ (−Methanol) |
| N/D | NeuAc•Hex$_5$•HexNAc$_4$•Fuc [M + Na]⁺ (undermethylated) |
| 2605.8 | NeuAc•Hex$_5$•HexNAc$_4$•Fuc [M + Na]⁺ |
| 2635.9 | NeuGc•Hex$_5$•HexNAc$_4$•Fuc [M + Na]⁺ |
| 2779.9 | NeuAc•Hex$_5$•HexNAc$_4$•Fuc$_2$ [M + Na]⁺ |
| 2911.0 | NeuAc$_2$•Hex$_5$•HexNAc$_4$•Fuc⁺ (A-type ion) |
| 2952.9 | NeuAc$_2$•Hex$_5$•HexNAc$_4$•Fuc [M + Na]⁺ (undermethylated) |
| 2966.9 | NeuAc$_2$•Hex$_5$•HexNAc$_4$•Fuc [M + Na]⁺ |
| 2996.9 | NeuAc•NeuGc•Hex$_5$•HexNAc$_4$•Fuc [M + Na]⁺ |
| 3055.0 | NeuAc•Hex$_6$•HexNAc$_5$•Fuc [M + Na]⁺ |
| 3140.9 | NeuAc$_2$•Hex$_5$•HexNAc$_4$•Fuc$_2$ [M + Na]⁺ |
| 3315.9 | NeuAc$_2$•Hex$_5$•HexNAc$_4$•Fuc$_3$ [M + Na]⁺ |
| 3416.1 | NeuAc$_2$•Hex$_6$•HexNAc$_5$•Fuc [M + Na]⁺ |
| 3590.9 | NeuAc$_2$•Hex$_6$•HexNAc$_5$•Fuc$_2$ [M + Na]⁺ |
| 3779.0 | NeuAc$_3$•Hex$_6$•HexNAc$_5$•Fuc [M + Na]⁺ |
| 3810.9 | NeuAc$_2$•NeuGc•Hex$_6$•HexNAc$_5$•Fuc [M + Na]⁺ |
| 3866.1 | NeuAc$_2$•Hex$_7$•HexNAc$_6$•Fuc [M + Na]⁺ |
| 4227.9 | NeuAc$_3$•Hex$_7$•HexNAc$_6$•Fuc [M + Na]⁺ |

Conclusions

MALDI-MS and FAB-MS analysis of the permethylated N-glycans of IFN-β-1a bulk samples obtained by the new process showed the following core-fucosylated carbohydrate structures (non-fucosylated glycans were not observed):

Major Glycoforms:

Monosialylated biantennary structure (NeuAc Hex$_5$.HexNAc$_4$.Fuc)

Disialylated biantennary structure (NeuAc$_2$ Hex$_5$.HexNAc$_4$.Fuc)

Minor Glycoforms:

Non sialylated biantennary structure (Hex$_5$.HexNAc$_4$.Fuc)

Disialylated triantennary structure or disialylated biantennary with N-acetyl lactosamine repeat structures (NeuAc$_2$.Hex$_6$.HexNAc$_5$.Fuc)

Trisialylated triantennary structure (NeuAc$_3$.Hex$_6$.HexNAc$_5$.Fuc)

Trisialylated triantennary with N-acetyl lactosamine repeat structures or trisialylated tetrantennary structures (NeuAc$_3$.Hex$_7$.HexNAc$_6$.Fuc)

Disialylated and monosialylated biantennary structure with two fucose units (NeuAc.Hex$_5$.HexNAc$_4$.Fuc$_2$, and NeuAc$_2$.Hex$_5$.HexNAc$_4$.Fuc$_2$)

Disialylated biantennary structure with three fucose units (NeuAc$_2$.Hex$_5$.HexNAc$_4$.Fuc$_3$)

Nanospray MS/MS of the permethylated glycans confirmed the detection of trace levels of NeuAc$_2$.Hex$_5$.HexNAc$_4$.Fuc$_2$ oligosaccharides in all samples while traces of NeuAc$_2$.Hex$_5$.HexNAc$_4$.Fuc$_3$ were observed only in IFN-β-1a from the process of the present invention.

Linkage analyses confirmed the expected monosaccharides detected with the FAB-MS data.

Finally, in the IFN-β-1a product obtained from the new process, the detailed FAB-MS analysis of the tryptic and chymotryptic peptides indicated the presence of N-glycan linkage at Asn-80.

The relative abundance of N-glycolylneuraminic acid was calculated from the peak heights of signals in the permethylated N-linked glycan FAB and MALDI-MS data.

The N-acetylneuraminic acid:N-glycolylneuraminic acid ratio was 31.7:1.0 in a sample and suggest that 3.1% of the sialic acid is N-Glycolylneuraminic acid. These results are in agreement with similar levels (5%) obtained for natural human interferon produced by human fibroblasts. As expected the IFN-β-1a glycoforms contain mainly N-acetylneuraminic acid like most human glycoproteins.

REFERENCES

1. Altschul S F et al, *J Mol Biol,* 215, 403-410, 1990
2. Altschul S F et al, *Nucleic Acids Res.,* 25:389-3402, 1997
3. Barber, M., Bordoli, R. S., Sedgwick, R. D. and Tyler A. N. (1981) *Chem. Commun.,* 325-327
4. Morris, H. R., Panico, M. and Taylor W. (1983) *Biochem. Biophys. Res. Commun.,* 117, 299-305.
5. Chernajovsky et al., Efficient Constitutive Production of Human Fibroblast interferon by Hamster Cells Transformed with the IFN-β Gene Fused to an SV40 Early Promoter, DNA, vol. 3, 1984, pp. 297-308
6. Chomczynski, P. and Sacchi, N. Anal. Biochem. 162:156-159, 1987
7. Clonis, Y. D., Atkinson, A., Bruton, C. J., and Lowe, C. R. (1987). "*Reactive Dyes in Protein and Enzyme Technology.*" stockton Press, New York.
8. Conradt et al., Structure of the carbohydrate moiety of human interferon beta secreted by a recombinant chinese hamster ovary cell line, jbc, vol 262, pp. 14600-14605, 1987.
9. Costello, C. E. (1997) *Biophys. Chem.,* 68, 173-188
10. Cummings, R. D. 1999. Structure and function of the selectin ligand PSGL-1. Braz. J. Med. Biol. Res. 32: 519-528.
11. Dell A. and H. Morris 2001. Glycoprotein structure determination by mass spectrometry. Science 291: 2351-2356
12. Derynk R. et al., *Nature* 285, 542-547, 1980;
13. Devereux J et al, *Nucleic Acids Res,* 12, 387-395, 1984
14. Domon, B. and Costello, C E (1988), *Biochemistry* 27, 1534-1543.
15. Fenn, J. B., Mann, M., Meng, C. K., Wong, S. F. and Whitehouse, C. M., (1989) *Science,* 246, 64-70.
16. Grantham et al., *Science,* Vol. 185, pp. 862-864 (1974)
17. Graham F L and Van Der E B A J A new technique for the assay of infectivity of human adenovirus 5 DNA. Virology 52:456-467, 1973; Busslinger M, Moschonas N, and Flavell R A b⁺ Thalassemia. Aberrant splicing results from a single point mutation in an intron. Cell 27:289-298, 1981
18. Gray, G. R., (1990) *Methods Enzymol.* 193, 573-587.
19. Harvey D. J., (2000) *J. Mass Spectrom.,* 35, 1178-1190
20. Hillenkamp, F., Karras, M., Beavis, R. C., Chait, B. T. (1991) *Anal. Chem.* 63, 1193-1203.

21. Innis M A, McCormick F. Procedures for expression, modification, and analysis of human fibroblast interferon (IFN-beta) genes in heterologous cells. Methods Enzymol. 1986; 119:397-403.
22. Kao, F.-T., and Puck, T. T., Genetics of Somatic mammalian cells, VII. Induction and isolation of nutritional mutants in chinese hamster cells Proc. Natl. Acad. Sci. USA 60, 1275-1281, 1968
23. Kaufman R and Sharp P. Amplification and expression of sequences cotransfected with a modular dihydrofolate reductase complementary DNA gene. Journal of Molecular Biology 159:601-621, 1982
24. Martinez G, Shaw E M, Carillo M and Zanuy S. Protein salting-out method applied to genomic DNA isolation from fish whole blood. Biotechniques 24(2): 238-239, 1998.
25. Mory et al. European J. Biochem. 120, 197-202 (1981)
26. Puck, J. Exp. Med. 108, 945, 1958
27. Reiser W and Hauser H. Recombinant human interferon beta from mammalian cell lines. Arzneimittelforschung/Drug Research 37 (I), 4, 482-485 (1987)
28. Runkel et al., Structural and Functional Differences Between Glycosylated and Non-glycosylated Forms of Human interferon beta (IFN-beta), Pharm. Res., vol 15, 1998, pp. 641-9.
29. Sambrook, J., Fritsch, E. F., Molecular Cloning: A laboratory manual. Cold Spring Harbor Laboratory Press, Cold Spring Harbor, N.Y., 1989
30. Smith and Waterman J Mol Biol, 147,195-197, 1981, Advances in Applied Mathematics, 2, 482-489, 1981.
31. Tarentino, A. L., Gomez, C. M., and Plummer, T. H. Jr (1985) *Biochemistry,* 24, 4665-4671.
32. Urlaub G and Chasin L A Isolation of chinese hamster cell mutants deficient in dihydrofolate reductase activity. Proc Natl Acad Sci USA 77(7):4216-4220, 1980).
33. Wilm, M., Mann, M (1996), *Anal. Chem.* 68, 1-8.
34. Youcefi et al., Am J Clin Pathol. 1985 June; 83(6):735-40

We claim:

1. A process for the manufacturing of glycosylated recombinant human interferon beta, comprising culturing a human interferon beta producing cell in a serum-free medium, said culturing comprising a growth phase I, a growth phase II and a production phase, wherein growth phase I is carried out at about 37° C., growth phase II is carried out at about 35° C., and the production phase is carried out at about 33° C., said serum-free medium comprising:
   a) about 10 to about 30 mM HEPES;
   b) about 0.5 to about 3 mM Proline;
   c) about 5500 to about 7000 mg/L sodium chloride; and
   d) N-acetyl cysteine alone or in combination with zinc.

2. The process according to claim 1, said serum-free medium comprising:
   a) about 10 to about 30 mM HEPES;
   b) about 0.5 to about 3 mM Proline; and
   c) about 5500 to about 7000 mg/L sodium chloride: and
   d) N-acetyl c swine alone.

3. The process according to claim 2, said serum-free medium further comprising about 10 to about 20 mg/L phenol red.

4. The process according to claim 1, wherein the process is a perfusion process with a dilution rate ranging from about 1 to about 10.

5. The process according to claim 4, wherein the dilution rate is increased within the first two to three weeks of cell culture from an initial value of about 1 to 2 per day to a value of about 7 to 10 per day.

6. The process according to claim 1, further comprising:
   a) subjecting the medium containing human interferon beta to affinity chromatography and eluting said human interferon beta;
   b) subjecting the human interferon beta containing eluate to cation exchange chromatography and eluting said human interferon beta; and
   c) subjecting the eluate of the cation exchange chromatography to hydrophobic chromatography by RP-HPLC and eluting said human interferon beta.

7. The process according to claim 6, comprising, before step (a), clarifying of the medium by filtration.

8. The process according to claim 7, further comprising:
   d) performing ultrafiltration and dialysis;
   e) subjecting the dialysate to size exclusion chromatography; and
   f) subjecting the eluate of the size exclusion chromatography to microfiltration.

9. The process according to claim 6, wherein step (a) is carried out on Blue Sepharose and step (b) is carried out on Carboxymethyl Sepharose.

10. The process according to claim 1, wherein said human interferon beta producing cell comprises:
   a) a nucleic acid comprising a human interferon beta coding sequence functionally linked to a SV40 T Ag early polyadenylation region, wherein the nucleic acid does not comprise the human interferon beta polyadenylation signal;
   b) a nucleic acid comprising a human interferon beta coding sequence functionally linked to a SV40 T Ag early polyadenylation region, wherein the nucleic acid does not comprise the human interferon beta polyadenylation signal and wherein said nucleic acid does not comprise the human interferon beta 3' UTR;
   c) a nucleic acid comprising a SV40 promoter/enhancer functionally linked to a human interferon beta coding sequence, wherein the human interferon beta coding sequence is functionally linked to the SV40 T Ag early polyadenylation region and the nucleic acid does not comprise the human interferon beta polyadenylation signal or the human interferon beta 3' UTR;
   d) a nucleic acid according to a), b) or c), wherein said nucleic acid further comprises a mouse dihydrofolate reductase (DHFR) gene;
   e) a nucleic acid according to d), wherein said mouse DHFR gene is functionally linked to a SV40 T Ag polyA-containing early polyadenylation region; or
   f) a nucleic acid according to e), further comprising a SV40 promoter/enhancer functionally linked to the mouse DHFR gene.

11. The method according to claim 1, wherein growth phase I is carried out at about 37° C. until the glucose consumption rate (GCR) is greater than or equal to $2.0\pm1.0$ grams per liter per day $(g \cdot L^{-1} \cdot d^{-1})$.

12. The method according to claim 1, wherein growth phase II is carried out at about 35° C. until the GCR is greater than or equal to $8.0\pm0.5$ grams per liter per day $(g \cdot L^{-1} \cdot d^{-1})$.

13. The method according to claim 1, wherein growth phase I is carried out at about 37° C. until the glucose consumption rate (GCR) is greater than or equal to $2.0\pm1.0$ grams per liter per day $(g \cdot L^{-1} \cdot d^{-1})$ and growth phase II is carried out at about 35° C. until the GCR is greater than or equal to $8.0\pm0.5$ grams per liter per day $(g \cdot L^{-1} \cdot d^{-1})$.

14. The method according to claim 1, wherein said serum-free medium comprises 20 mM HEPES, 1 mM proline, 15 mg/L phenol red and 6150 mg/L NaCl.

15. The method according to claim 1, said serum-free medium comprising:
   a) about 10 to about 30 mM HEPES;
   b) about 0.5 to about 3 mM Proline;
   c) about 5500 to about 7000 mg/L sodium chloride; and
   d) N-acetyl cysteine in combination with zinc.

16. The method according to claim 1, wherein said serum-free medium comprises 20 mM HEPES, 1 mM proline, 15 mg/L phenol red, 6150 mg/L NaCl and N-acetyl cysteine.

17. The method according to claim 1, wherein said serum-free medium comprises 20 mM HEPES, 1 mM proline, 15 mg/L phenol red, 6150 mg/L NaCl and N-acetyl cysteine in combination with zinc.

* * * * *

UNITED STATES PATENT AND TRADEMARK OFFICE
CERTIFICATE OF CORRECTION

| | | |
|---|---|---|
| PATENT NO. | : 8,993,724 B2 | Page 1 of 1 |
| APPLICATION NO. | : 13/159864 | |
| DATED | : March 31, 2015 | |
| INVENTOR(S) | : Dina Fischer et al. | |

It is certified that error appears in the above-identified patent and that said Letters Patent is hereby corrected as shown below:

In the specification

Column 3,
Line 17, "(Darter)." should read --(Darfler).--.

Signed and Sealed this
Fifteenth Day of December, 2015

Michelle K. Lee
*Director of the United States Patent and Trademark Office*